(12) United States Patent
MacMahon et al.

(10) Patent No.: US 11,833,049 B2
(45) Date of Patent: Dec. 5, 2023

(54) SELF-ADJUSTING DEVICE

(71) Applicants: Chine, LLC, Exeter, NH (US); John MacMahon, Exeter, NH (US); Evan Anderson, Woodside, CA (US); Greg C. Liu, Sunnyvale, CA (US)

(72) Inventors: John MacMahon, Exeter, NH (US); Evan Anderson, Woodside, CA (US); Greg C. Liu, Sunnyvale, CA (US)

(*) Notice: Subject to any disclaimer, the term of this patent is extended or adjusted under 35 U.S.C. 154(b) by 323 days.

(21) Appl. No.: 16/964,974

(22) PCT Filed: Jan. 25, 2019

(86) PCT No.: PCT/US2019/015302
§ 371 (c)(1),
(2) Date: Jul. 25, 2020

(87) PCT Pub. No.: WO2019/148048
PCT Pub. Date: Aug. 1, 2019

(65) Prior Publication Data
US 2021/0045876 A1 Feb. 18, 2021

Related U.S. Application Data

(60) Provisional application No. 62/622,831, filed on Jan. 27, 2018, provisional application No. 62/622,830, (Continued)

(51) Int. Cl.
*A61F 2/24* (2006.01)
*A61B 17/10* (2006.01)
(Continued)

(52) U.S. Cl.
CPC .......... *A61F 2/2481* (2013.01); *A61B 17/068* (2013.01); *A61B 17/10* (2013.01);
(Continued)

(58) Field of Classification Search
CPC ...... A61F 2/2481; A61F 2/2451; A61F 2/246; A61F 2210/0033; A61F 2250/0002;
(Continued)

(56) References Cited

U.S. PATENT DOCUMENTS 5,048,536 A * 9/1991 McEwen ............ A61B 17/1355
600/587
5,835,996 A 11/1998 Hashimoto et al.
(Continued)

FOREIGN PATENT DOCUMENTS

EP 1646332 3/2005
WO 2019148048 8/2019

OTHER PUBLICATIONS

Boehmer et al., "A Multisensor Algorithm Predicts Heart Failure Events in Patients With Implanted Devices", JACC Heart Failure, vol. 5, No. 3, 2017, pp. 216-225, (Mar. 2017).
(Continued)

*Primary Examiner* — Paul B Prebilic
(74) *Attorney, Agent, or Firm* — Law Office of Alan W. Cannon

(57) ABSTRACT

A self-adjusting device configured to be placed in contact with tissue/organ and apply mechanical force to the tissue/organ to achieve an improvement of functioning of the tissue/organ. The self-adjusting capabilities can be carried out by three functional subsystems that can be packaged either in a single, integrated system or in separate modules. A sensing subsystem senses the tissue/organ and sends at least one type of sensing signal characteristic of functioning of the tissue/organ to a controlling subsystem. The controlling subsystem processes the signal with an algorithm to determine if a configuration of the device needs to be changed or a force applied to the tissue/organ needs to be changed. An actuating subsystem can be controlled by the controlling subsystem to affect the configuration/force
(Continued)

change when needed. A feedback loop is provided to keep the controlling subsystem up to date as to the state of the actuating subsystem.

23 Claims, 19 Drawing Sheets

Related U.S. Application Data filed on Jan. 27, 2018, provisional application No. 62/622,827, filed on Jan. 27, 2018.

(51) Int. Cl.
*A61B 90/00* (2016.01)
*A61B 17/068* (2006.01)
*A61B 17/00* (2006.01)
*A61B 17/28* (2006.01)
*A61B 17/064* (2006.01)

(52) U.S. Cl.
CPC .............. *A61B 90/06* (2016.02); *A61F 2/246* (2013.01); *A61F 2/2442* (2013.01); *A61F 2/2451* (2013.01); *A61F 2/2466* (2013.01); *A61F 2/2478* (2013.01); *A61B 17/064* (2013.01); *A61B 17/2812* (2013.01); *A61B 2017/00243* (2013.01); *A61B 2017/00398* (2013.01); *A61B 2017/00407* (2013.01); *A61B 2017/00473* (2013.01); *A61B 2017/00738* (2013.01); *A61B 2017/00858* (2013.01); *A61B 2017/0649* (2013.01); *A61B 2090/061* (2016.02); *A61B 2090/0801* (2016.02); *A61F 2002/2484* (2013.01); *A61F 2210/0033* (2013.01); *A61F 2210/0076* (2013.01); *A61F 2220/0016* (2013.01); *A61F 2220/0025* (2013.01); *A61F 2220/0033* (2013.01); *A61F 2220/0083* (2013.01); *A61F 2230/0013* (2013.01); *A61F 2230/0023* (2013.01); *A61F 2250/001* (2013.01); *A61F 2250/0002* (2013.01); *A61F 2250/0003* (2013.01); *A61F 2250/0004* (2013.01); *A61F 2250/006* (2013.01); *A61F 2250/0007* (2013.01); *A61F 2250/0029* (2013.01); *A61F 2250/0036* (2013.01); *A61F 2250/0064* (2013.01)

(58) Field of Classification Search
CPC ........ A61F 2250/0006; A61F 2250/001; A61F 2250/006
See application file for complete search history.

(56) References Cited

U.S. PATENT DOCUMENTS

| | | |
|---|---|---|
| 6,246,241 B1 | 6/2001 | Newland |
| 6,650,940 B1 | 11/2003 | Zhu et al. |
| 7,011,682 B2 * | 3/2006 | Lashinski ............ A61F 2/2466 623/2.37 |
| 7,853,327 B2 | 12/2010 | Patangay et al. |
| 8,647,254 B2 | 2/2014 | Callas et al. |
| 9,211,115 B2 | 12/2015 | Annest et al. |
| 9,700,726 B2 | 7/2017 | Stahmann et al. |
| 9,724,194 B2 | 8/2017 | Callas et al. |
| 9,795,481 B2 | 10/2017 | Callas et al. |
| 10,485,663 B2 | 11/2019 | Callas et al. |
| 2004/0010180 A1 | 1/2004 | Scorvo |
| 2004/0260346 A1 | 12/2004 | Overall et al. |
| 2005/0060030 A1 * | 3/2005 | Lashinski ............ A61F 2/2466 623/2.37 |
| 2005/0209649 A1 | 9/2005 | Ferek-petric |
| 2006/0041183 A1 | 2/2006 | Massen et al. |
| 2006/0178586 A1 | 8/2006 | Dobak, III |
| 2007/0112326 A1 * | 5/2007 | Bosshard ............ A61M 5/145 604/500 |
| 2008/0119891 A1 | 5/2008 | Miles et al. |
| 2009/0305212 A1 | 12/2009 | McKenzie et al. |
| 2010/0010538 A1 | 1/2010 | Juravic et al. |
| 2012/0323314 A1 | 12/2012 | Callas et al. |
| 2019/0110696 A1 * | 4/2019 | Benkowski .......... A61B 5/0031 |
| 2019/0231528 A1 * | 8/2019 | MacMahon .......... A61F 2/2451 |
| 2020/0015972 A1 | 1/2020 | Callas et al. |

OTHER PUBLICATIONS

"Boston Scientific Announces Positive Results of HeartLogicTM Heart Failure Diagnostic Service", http://news.bostonscientific.com/2016-11-16-Boston-Scientific-Annnounces-Positive-Results-Of-HeartLogic-Heart-Failure-Diagnostic-Service, Nov. 16, 2016, pp. 1-7.

Grayburn et al., "Proportionate and Disproportionate Functional Mitral Regurgitation", JACC Cardiovascular Imaging, 2018, pp. 1-10, (Dec. 2018).

International Search Report re PCT/US2019/015302, dated Jun. 28, 2019.

* cited by examiner

SELF-ADJUSTING DEVICE

CROSS-REFERENCE

This application is a 371 of International Application No. PCT/US2019/015302, filed Jan. 25, 2019, which claims the benefit of U.S. Provisional Application Nos. 62/622,827; 62/622,830; and 62/622,831, each of which were filed on Jan. 27, 2018. Each of PCT/US2019/015302; U.S. Provisional Application No. 62/622,827; U.S. Provisional Application No. 62/622,830; and U.S. Provisional Application No. 62/622,831 are hereby incorporated herein, in their entireties, by reference thereto and to which application we claim priority under 35 USC § 119.

INCORPORATION BY REFERENCE

All publications and patent applications mentioned in this specification are herein incorporated by reference to the same extent as if each individual publication or patent application was specifically and individually indicated to be incorporated by reference. This specification specifically incorporates US Patent Application Publication Nos. 2010/0004504 A1 and 2012/0323314 A1 herein, in their entireties, by reference thereto. Also specifically incorporated by reference in their entireties, are U.S. Provisional Application Ser. Nos. 62/622,831 and 62/622,830, as noted above. Further, this specification specifically incorporates the following applications in their entireties: U.S. application Ser. No. 16/258,525, titled "Atraumatic Adjustment or Replacement of a Device for Treating Valve Regurgitation", filed Jan. 25, 2019; International (PCT) Application No. PCT/US2019/015300, titled "Epicardial Valve Repair System", filed Jan. 25, 2019; and U.S. application Ser. No. 16/258,519, titled "Manually Adjustable Device", filed Jan. 25, 2019.

FIELD OF THE INVENTION

The disclosure is directed to medical devices, assemblies and methods for reshaping tissue/organ of a patient. More particularly the disclosure is directed to medical devices, assemblies and methods for reshaping a portion of a heart. More particularly, the disclosure is directed to devices, assemblies and methods for self-adjustment of forces applied for reshaping.

BACKGROUND OF THE INVENTION

There is broad prevalence of various organ diseases directly related to mechanical compromise of the organ tissues and/or functions. Various ones of these conditions are degenerative and progressive, for example degenerative mitral valve regurgitation. The mitral valve is located between the left atrium and the left ventricle of the heart. During normal operation, the mitral valve opens during diastole, allowing blood to flow from the left atrium into the left ventricle. During systole, the mitral valve closes, causing high pressure blood to exit the left ventricle through the aorta. Mitral valve regurgitation is a cardiac condition in which the posterior leaflet of the mitral valve does not fully contact the anterior leaflet of the valve during systole, thus a gap remains between the leaflets of the mitral valve during systole. The gap remaining between the leaflets allows retrograde blood flow to pass from the left ventricle into the left atrium through the mitral valve. Thus, mitral regurgitation reduces the volume of blood pumped out of the heart to the aorta during each cardiac cycle, thus reducing the efficiency of the heart. Mitral regurgitation may exist for any of several reasons, including congenital malformations of the valve, ischemic disease, or effects of cardiomyopathy, such as dilated (congestive) cardiomyopathy (i.e., enlarging of the heart). Recent randomized trials in heart failure and the MitraClip device found that reducing mitral regurgitation arrested the dilation of the left ventricle, common in the heart failure cycle. Grayburn et al, "Proportionate and Disproportionate Functional Mitral Regurgitation" JACC: Cardiovascular Imaging, 2018 cited that longevity and improved quality of life paralleled left ventricular volume reductions. It is reasonable that designs that reduce both mitral regurgitation and cardiac volume may have profound clinical benefits.

Conventional techniques for treating dysfunctions of the mitral valve typically include highly invasive, open heart surgical procedures in order to replace or repair the dysfunctioning mitral valve. Some surgical procedures include the implantation of a replacement valve (e.g., animal valve or artificial mechanical valve). Other techniques include the use of annuloplasty rings which are surgically placed around the annulus of the mitral valve within the chamber of the heart and sutured into place. The presence of the annuloplasty ring alters the geometry of the annulus of the mitral valve in order to improve coaptation of the leaflets of the valve. Epicardial clips have also been proposed and used to alter the geometry of the annulus of the mitral valve. Another surgical technique which requires accessing one or more chambers of the heart is leaflet coaptation. Leaflet coaptation (e.g., Alfieri edge-to-edge repair) is a surgical procedure in which the valve leaflets are sutured together (e.g., bow-tie suture) to improve coaptation of the leaflets. A further surgical technique includes extending a tensioning cord across a chamber of the heart to alter the geometry of the heart chamber. The tensioning cord, which extends through a chamber of the heart, and thus is in contact with blood in the heart chamber, pulls opposing walls of the heart toward one another to reduce heart wall tension and/or reposition the papillary muscles within the chamber. These techniques typically require opening the heart and/or entering one or more of the chambers of the heart to gain direct access to the mitral valve.

All of the aforementioned treatments are static approaches to treatment of the disease. That is, the configuration of the devices used to treat the disease remain as fixed at the time of performing the procedure. However, many, if not most of diseases treated, including mitral regurgitation, are degenerative, and may worsen over time. Worsening of conditions may require additional reshaping forces to be applied to maintain abatement of mitral regurgitation or other malady being treated.

Therefore, it may be desirable to devise a less invasive technique for treatment of diseases such as mitral valve regurgitation, wherein the treatment applied may dynamically change after the initial treatment applied during a surgical procedure.

It may further be desirable to provide solutions in which dynamic changes of treatment applied occur automatically, such as by use of a self-adjusting device.

It may be desirable to devise a device, assembly and/or method useful in altering and/or reshaping the annulus of the mitral valve and/or the ventricle of a heart without the need to gain access to the interior of the heart, and which can self-adjust to change conditions applied to alter and/or reshape the annulus and/or ventricular geometry so as to maintain satisfactory abatement or reduction of mitral regurgitation. Additionally, adjustments of chordae geometry and/or artificial chordae lengths based on feedback are of importance.

It may be desirable to provide solutions in which in vivo, real time functional sensing can be performed.

It may be desirable to provide solutions in which closed loop feedback from a sensing circuit to an actuation circuit are provided to facilitate self-adjustment of a device.

It may further be desirable to provide devices which are self-powering through energy generation and storage derived from organ/tissue motion.

It may further be desirable to provide devices that can be minimally invasively implanted and/or which allow procedural reversibility.

SUMMARY OF THE INVENTION

The present invention provides a self-adjusting device configured to be placed in contact with tissue/organ and apply mechanical force to the tissue/organ to achieve an improvement of functioning of the tissue/organ. The self-adjusting capabilities can be carried out by three functional subsystems and a feedback loop so that real-time (or near real-time) monitoring of the tissue/organ and adjustment of the device can be carried out to maintain the tissue/organ functioning as well as can be achieved by alteration of mechanical forces thereto.

In some embodiments, the device can be packaged either in a single, integrated system or in separate modules. A sensing subsystem may be provided to sense the tissue/organ and send at least one type of sensing signal characteristic of functioning of the tissue/organ to a controlling subsystem. The controlling subsystem processes the signal with an algorithm to determine if a configuration of the device needs to be changed or a force applied to the tissue/organ needs to be changed. An actuating subsystem can be controlled by the controlling subsystem to affect the configuration/force change when needed. A feedback loop is provided to keep the controlling subsystem up to date as to the state of the actuating subsystem.

Thus, treatment and relief of various conditions of tissue/organ can be improved through systems that sense and adapt to the progression of and/or variation in mechanical compromise of the organ function. Further, as these chronic conditions progress, treatment regimens can benefit from reversible procedures and/or devices.

In one aspect of the present invention, an epicardial device for reducing or preventing regurgitation of blood through a valve of a heart is provided that includes: a main body having a surface adapted to be contacted to an epicardial surface of the heart; a sensor on or in said surface adapted to sense a signal characteristic of a function of the valve; an actuator in a portion of the main body which, when actuated, changes a conformation of the main body; and a controller configured to receive the signal, process the signal, and, control actuation of the actuator when it is determined that an unacceptable level of regurgitation is occurring.

In at least one embodiment, the epicardial device is configured for reshaping an annulus of a mitral valve of the heart.

In at least one embodiment, the epicardial device is configured for reshaping one or more dimensions of a left ventricle of the heart.

In at least one embodiment, the epicardial device is configured for reshaping an annulus of a tricuspid valve of the heart.

In at least one embodiment, the epicardial device is configured for reshaping one or more dimensions of a right ventricle of the heart.

In at least one embodiment, an intraventricular device is configured for reshaping the chordae or artificial chordae of a mitral valve of the heart.

In at least one embodiment, the controller is configured to process the signal received from the sensor and control actuation of the actuator in real time.

In at least one embodiment, the sensor, the actuator and the controller are all contained in the main body.

In at least one embodiment, the sensor comprises an audio sensor configured to receive audio signals generated by functioning of the valve, and wherein the controller compares an audio signature of the valve characterized by electrical signals converted from the audio signals received by the audio sensor, with a normal audio signature characteristic of a valve with no regurgitation, to determine whether to actuate the actuator.

In at least one embodiment, the sensor comprises a motion sensor; wherein the motion sensor converts motion applied thereagainst by the epicardial surface of the heart in contact with the motion sensor, to an electrical signal characterizing the motion.

In at least one embodiment, the sensor comprises a motion sensor; wherein the motion sensor converts motion applied thereagainst by the epicardial surface of the heart in contact with the motion sensor, to an electrical signal for motion-driven electric power generation.

In at least one embodiment, the controller includes an energy conversion unit that converts the electrical signal from the motion sensor to electrical energy having requisite characteristics for charging an energy storage unit to power the controller and the actuator.

In at least one embodiment, the sensor comprises an electrical sensor configured to receive electrical signals generated by functioning of the valve or heart, and wherein the controller compares the electrical signals from the electrical sensor with a normal electrical signal characteristic of normal functioning of the valve with no regurgitation, to determine whether to actuate the actuator.

In at least one embodiment, the actuator comprises a bi-metallic, resistively heated actuator.

In at least one embodiment, the actuator comprises an expandable chamber.

In at least one embodiment, the actuator is motor driven.

In at least one embodiment, the main body comprises an anterior segment adapted to be contacted to an anterior surface of the heart, a posterior segment adapted to be contacted to a posterior surface of the heart and a lateral segment joining the anterior segment and the posterior segment.

In at least one embodiment, the epicardial device further includes an inferior segment extending from the main body in a direction transverse to a plane in which the anterior, lateral and posterior segments extend.

In at least one embodiment, the epicardial device further includes a second actuator located in the inferior segment.

In another aspect of the present invention, a device configured to be attached to a surface of a tissue or organ using a minimally-invasive procedure is provided. The device includes: a main body having a device surface adapted to be contacted to the tissue or organ; a sensor on or in the device surface adapted to sense a signal characteristic of a function of tissue or organ; an actuator in a portion of the main body which, when actuated, changes a conformation of the main body; and a controller configured to receive the signal, process the signal, and, control actuation of the actuator when it is determined that an unacceptable condition of functioning of the tissue or organ is occurring.

In at least one embodiment, the controller is configured to process the signal received from the sensor and control actuation of the actuator in real time.

In at least one embodiment, the sensor, the actuator and the controller are all contained in the main body.

In at least one embodiment, the sensor comprises an audio sensor configured to receive audio signals generated by functioning of the tissue or organ, and wherein the controller compares an audio signature of the tissue or organ characterized by electrical signals converted from the audio signals received by the audio sensor, with a normal audio signature characteristic of the tissue or organ with no regurgitation, to determine whether to actuate the actuator.

In at least one embodiment, the device further includes a motion sensor; wherein the motion sensor converts motion applied thereagainst by the tissue or organ in contact with the motion sensor, to an electrical signal for motion-driven electric power generation; and wherein the controller includes an energy conversion unit that converts the electrical signal from the motion sensor to electrical energy having requisite characteristics for charging an energy storage unit to power the controller and the actuator.

In at least one embodiment, the motion sensor further converts motion applied thereagainst by the tissue or organ to an electrical signal characterizing the motion.

In at least one embodiment, the actuator comprises a bi-metallic, resistively heated actuator.

In at least one embodiment, the actuator comprises an expandable chamber.

In another aspect of the present invention, a method of epicardial treatment of mitral regurgitation associated with the mitral valve of a heart is provided, the anatomy of the heart including an aorta, a pulmonary trunk, a superior vena cava, a transverse sinus, a left atrial appendage, and an oblique sinus. The method includes: providing a device having an anterior segment, an anterior end, a posterior segment, a posterior end and a lateral segment extending between the anterior segment and the posterior segment; positioning the anterior segment in the transverse sinus of the heart; positioning the posterior segment on or inferior to the atrioventricular groove of the heart, wherein the device reshapes the annulus of the mitral valve; and wherein the anterior and posterior ends are spaced apart from one another by a predetermined distance and remain separated by a gap or opening after the positionings; monitoring at least one of audio, electrical or motion of an epicardial surface of the heart contacted by the device; processing a signal received as a result of the monitoring and determining whether adjustment of the device is needed, based on the processing; and when it is determined that adjustment is needed, actuating an actuator of the device to reconfigure the device so that the anterior and posterior ends are spaced apart by a modified distance different from the predetermined distance.

In at least one embodiment, the monitoring, processing, determining and actuating are performed in real time.

In another aspect of the present invention, an epicardial device for reducing or preventing regurgitation of blood through a valve of a heart includes: a main body having a surface adapted to be contacted to an epicardial surface of the heart; and an actuator in a portion of said main body which, when actuated, changes a conformation of said main body; wherein said actuator is actuated upon receiving control signals from a controller via wired or wireless connection.

In at least one embodiment, the controller is configured to receive input from at least one sensor and, based upon the input, decide whether to actuate the actuator.

In at least one embodiment, the at least one sensor is provided with a system that includes the device and the controller.

In at least one embodiment, the at least one sensor is provided in a second device that is not part of a system that includes the epicardial device and the controller.

In at least one embodiment, the controller is integral with the device.

In at least one embodiment, the at least one sensor is integral with the device.

In at least one embodiment, the controller is configured to receive manual input from a user.

In at least one embodiment, the controller is configured so that the manual input overrides decision making resulting from automatic processing of the input from the at least one sensor.

These and other features of the invention will become apparent to those persons skilled in the art upon reading the details of the devices, systems and methods as more fully described below.

BRIEF DESCRIPTION OF THE DRAWINGS

The invention may be more completely understood in consideration of the following detailed description of various embodiments in connection with the accompanying drawings in which.

DETAILED DESCRIPTION OF THE INVENTION

Figure 1:
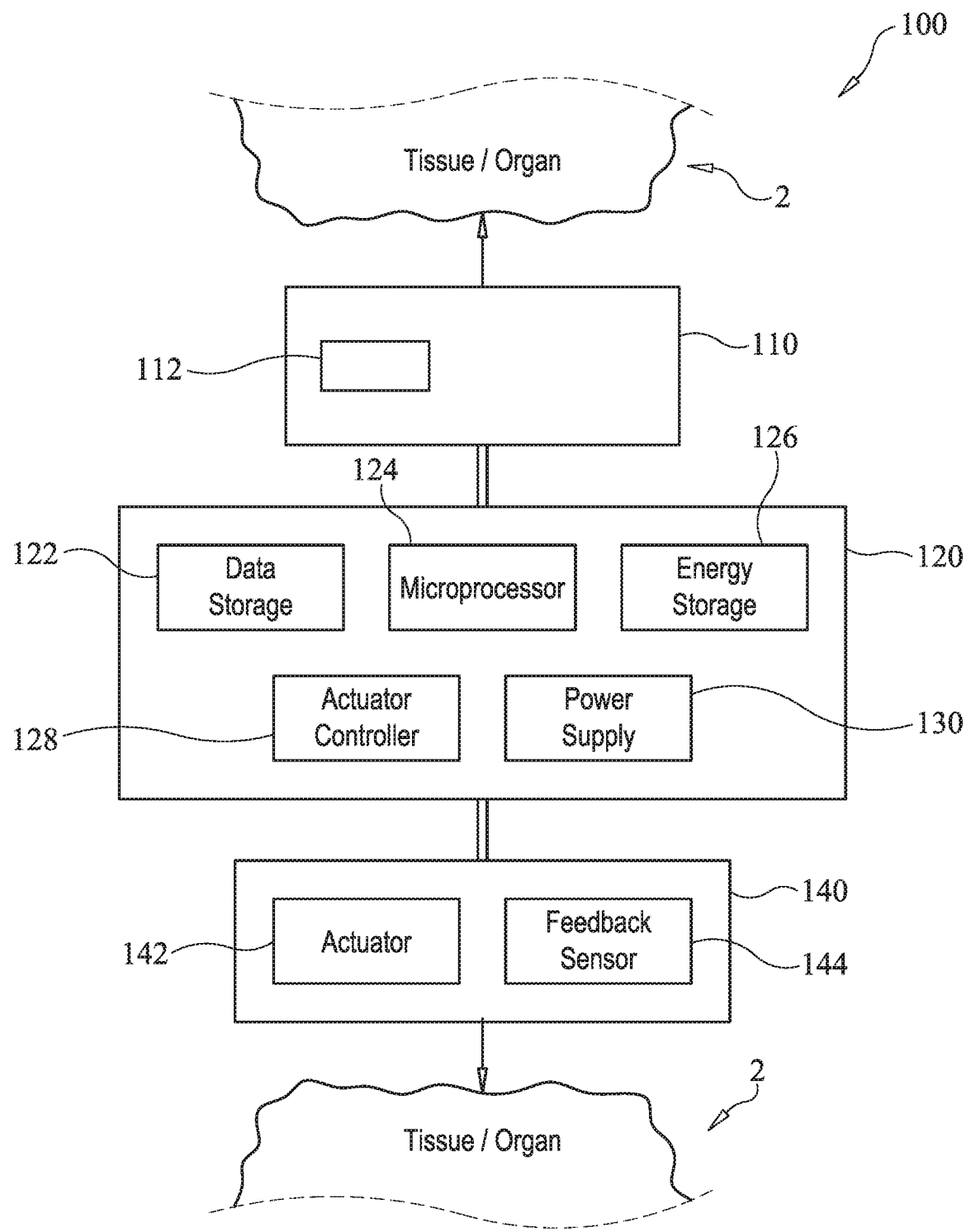
FIG. 1 is a schematic illustration of three functional subsystems or modules of a system according to an embodiment of the present invention.

Before the present devices, components and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Additionally the feedback may come from a secondary device that is providing some monitoring, as in the open source mode of communication from different implants, including but not limited to defibrillators and or personal health devices such as but not limited to smart watches.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a sensor includes a plurality of such sensors and reference to "the controller" includes reference to one or more controllers and equivalents thereof known to those skilled in the art, and so forth.

The publications discussed herein are provided solely for their disclosure prior to the filing date of the present application. Further, the dates of publication provided may be different from the actual publication dates which may need to be independently confirmed.

Definitions

As used in the specification and the appended claims, the term "anterior" is used in its anatomical sense to mean "toward the front, in front of, or the front surface of."

As used in the specification and the appended claims, the term "posterior" is used in its anatomical sense to mean "toward the back, in back of, or the back surface of."

As used in the specification and the appended claims, the term "superior" is used in its anatomical sense to mean "above, over top of, directed upward or toward the head."

As used in the specification and the appended claims, the term "inferior" is used in its anatomical sense to mean "below, underneath, directed downward or toward the feet."

As used in the specification and the appended claims, the term "lateral" is used in its anatomical sense to mean "a position or direction farther from the sagittal or median plane or midline of the body, to the side of, or the side surface of."

Detailed Description

The self-adjusting capabilities of the present invention can be carried out by three functional subsystems that can be packaged either in a single, integrated system or in separate modules. The description herein primarily focuses on single, integrated system embodiments. Alternatively, one or more of the three functional subsystems can be separated from or spaced apart from a device that houses one or more of the other three functional subsystems. Further alternatively, whether provided in a single integrated system or a system having one or more separate modules, the system can further be configured to communicate with other devices. For example the system can be configured to receive input from one or more monitoring devices that are not a part of the system. For example, the system could receive input from a separate heart rate monitor, a pacer, existing passive cardiac sensors, or another monitor that audibly monitors heart sounds. This ability to receive input is not limited to the devices specifically listed here, as virtually any other devices configured to monitor a condition that would be relevant to decision making by the system, could be received by the system. The input received from such an external device could be relied on solely as the sensing input needed by the system to decide whether to self-adjust, or, alternatively, the input received from the external device could be used in combination with sensing input generated from a sensing portion of the system. Further alternatively, the system could rely solely on sensing input generated by the system. Further optionally, the system could also be configured for two way communication with other devices that are not part of the system.

Figure 2:
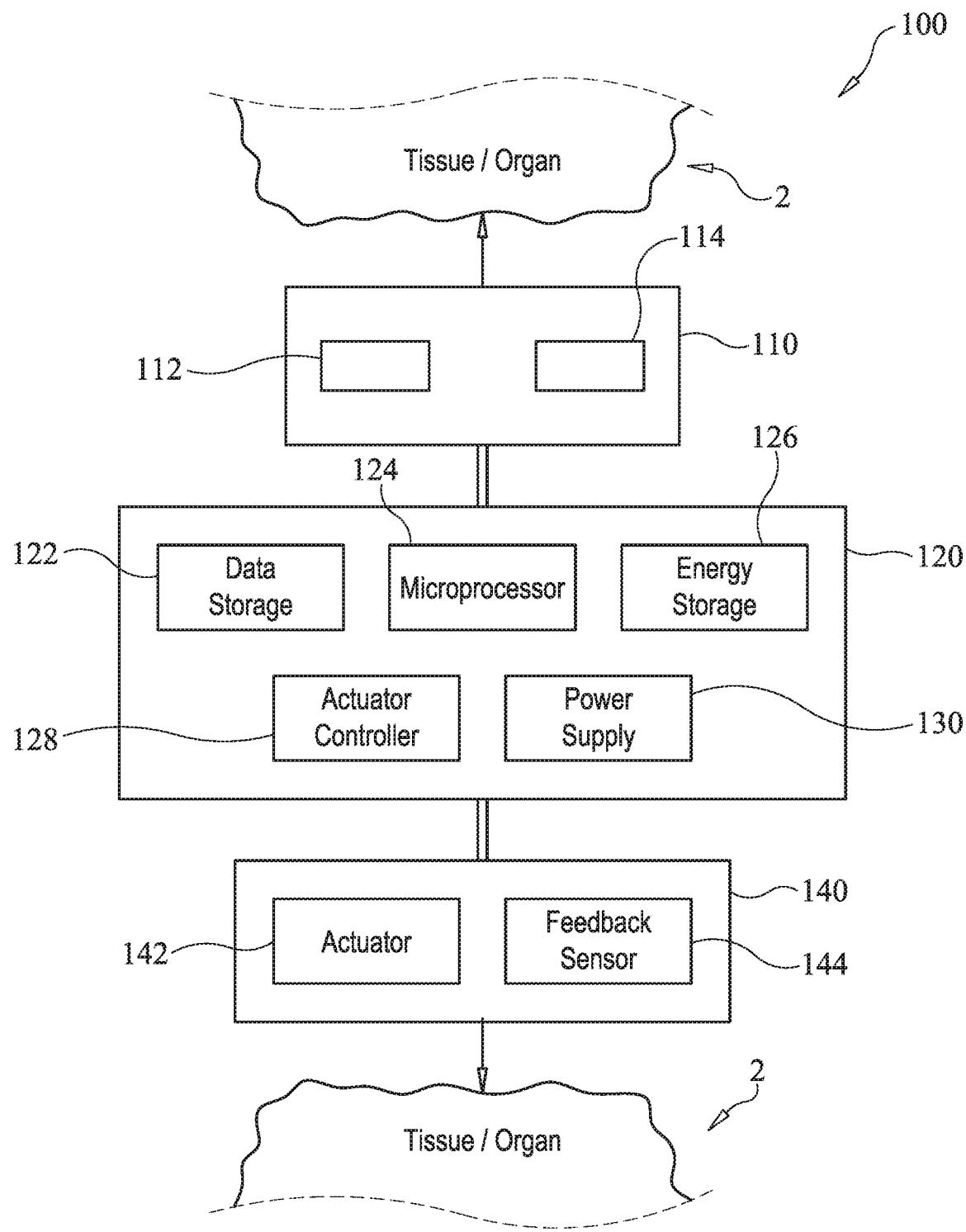
FIG. 2 is a schematic illustration of three functional subsystems or modules of a system according to another embodiment of the present invention.
Figure 3:
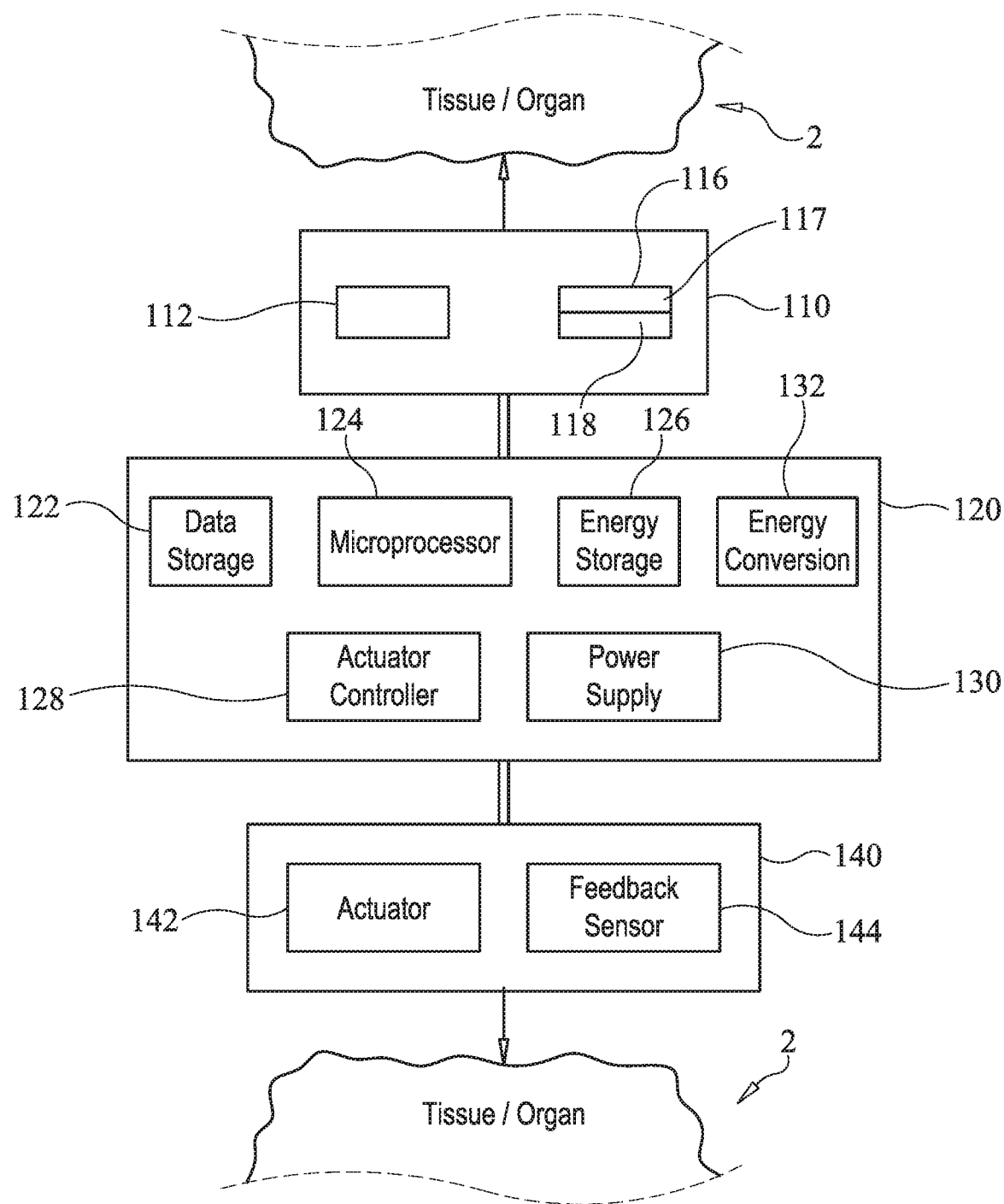
FIG. 3 is a schematic illustration of three functional subsystems or modules of a system according to another embodiment of the present invention.

FIG. 1 is a schematic illustration of the three functional subsystems or modules referred to above. A functional system 100 includes a sensing subsystem 110, a controlling subsystem 120 and an actuating subsystem 140. The subsystems 110, 120 and 140 are all in electrical communication with one another, preferably via hard wire, but alternatively, one or more systems could communicate wirelessly. Sensing subsystem 110 is configured to be placed in contact with tissue/organ 2 of a patient 1 being treated so as to directly sense a signal characteristic of the function of the tissue/organ 2. Sensing subsystem 110 includes at least one sensor for performing the sensing function. In one embodiment, an acoustic or audio sensor 112, such as a microphone or equivalent is provided to listen to audio signals from the tissue/organ 2 being treated. For example, the acoustic sensor 112 may directly detect heart sounds in the area of the mitral valve or other valve being treated. For example, in the case of treatment of mitral regurgitation, acoustic sensor 112 receives sounds generated by the flow of blood through the mitral valve. In another embodiment the sensor could include a sensor to generate echocardiographic images including Doppler for capture and processing similar to transesophageal or intracoronary echocardiography. FIG. 2 illustrates another embodiment in which an electrical sensor 114 is included in subsystem 110. For treatment of heart related maladies such as, but not limited to mitral regurgitation, the electrical sensor 114 directly detects voltage changes in the tissue itself in the form of analog signals that can be used for electrocardiogram (ECG) readings. FIG. 3 illustrates another embodiment in which a motion sensor 116 is included in subsystem 110. The function of motion sensor is described in the further description of FIG. 3 below. It is noted that other embodiments of sensing subsystem may include all of sensors 112, 114 and 116. Likewise, other embodiments may include only sensor 114 or only sensors 114 and 116.

Controlling subsystem 120 includes a microprocessor 124 that processes incoming signals from the sensing subsystem 110. An algorithm which may be stored in data storage 122 can be accessed by microprocessor 124 for use in comparing signals received from the sensing subsystem to "normal" signals stored in data storage so that a determination can be made as to whether adjustment of the device that the system controls is needed to alter the functioning of the tissue/organ 2 back toward normal functioning. Energy to operate the system is stored in energy storage 126, such as a battery. The energy storage 126 may be recharged by any of a number of techniques, including, but not limited to: electrical charging, wherein a lead wire extending from the system to a port in a patient in which the tissue/organ 2 is located, can be connected to an external source of electrical power to perform the charging; wireless charging, or the like. In the embodiment described for FIG. 3, energy is converted from motion of the tissue/organ 2 and/or patient 1 to restore the energy in energy storage 126. A power supply 130 is powered by the energy storage 126 and converts the stored energy to electrical energy having the appropriate voltage and current characteristics for operating the system 100.

Thus, the controlling subsystem 120 may include energy conversion, power supply, and controller modules, comprising a micro-controller, electrical energy conversion, storage, and supply units, and data storage. Controlling subsystem 120 may carry out any or all of the following functions: (1) receive acoustic/electrical/motion information from the sensing subsystem 110 and determining if there is a need for and level of mechanical reshaping of the tissue/organ 2 through an algorithm on the micro-controller; and (2) store the energy supplied by the sensing subsystem 110 and supplying that energy to the controller and actuating module, as well as any other power requiring features of the system 100.

In some embodiments, motion sensors may include one or both of: (1) Piezo-electric transducer(s) (PET) and (2) Inertial Measurement Unit(s) (IMU), especially accelerometer functions. The PET may translate kinetic energy from the pulsatile motion of the heart into electrical energy in the form of electrical potential changes. The IMU may detect changes in acceleration of the target tissue and convert the changes detected to digital signals.

When it is determined, after running the algorithm with the sensing signals received, that actuation of the actuator is needed, the microprocessor 124 instructs the actuator controller 128 to send actuation control signals to actuator 142 located in the actuating subsystem 140. The controlling subsystem determines the need for and level of displacement for the actuator(s) 142, which need is determined in direct response to the signals received from the sensing subsystem. The actuating subsystem 140 also directly contacts the tissue/organ 2, so that movement of the actuator directly changes the way in which in contacts the tissue/organ 2, such as by increase or decrease in force applied, change in the shape of footprint of the contact surface through which force is applied, etc. In the case of mitral regurgitation, the need for actuation can be determined in direct response to the audio signals received from audio sensor 112. The sound of blood passing forward through the mitral valve from the left atrium to the left ventricle is distinctly different from the sound of blood passing retrograde through the mitral valve from the left ventricle to the left atrium. Thus, when a signature sound of retrograde blood flow through the mitral valve is detected, the system actuates the actuator(s) 142 in an effort to reduce or eliminate the retrograde blood flow.

Figure 4:
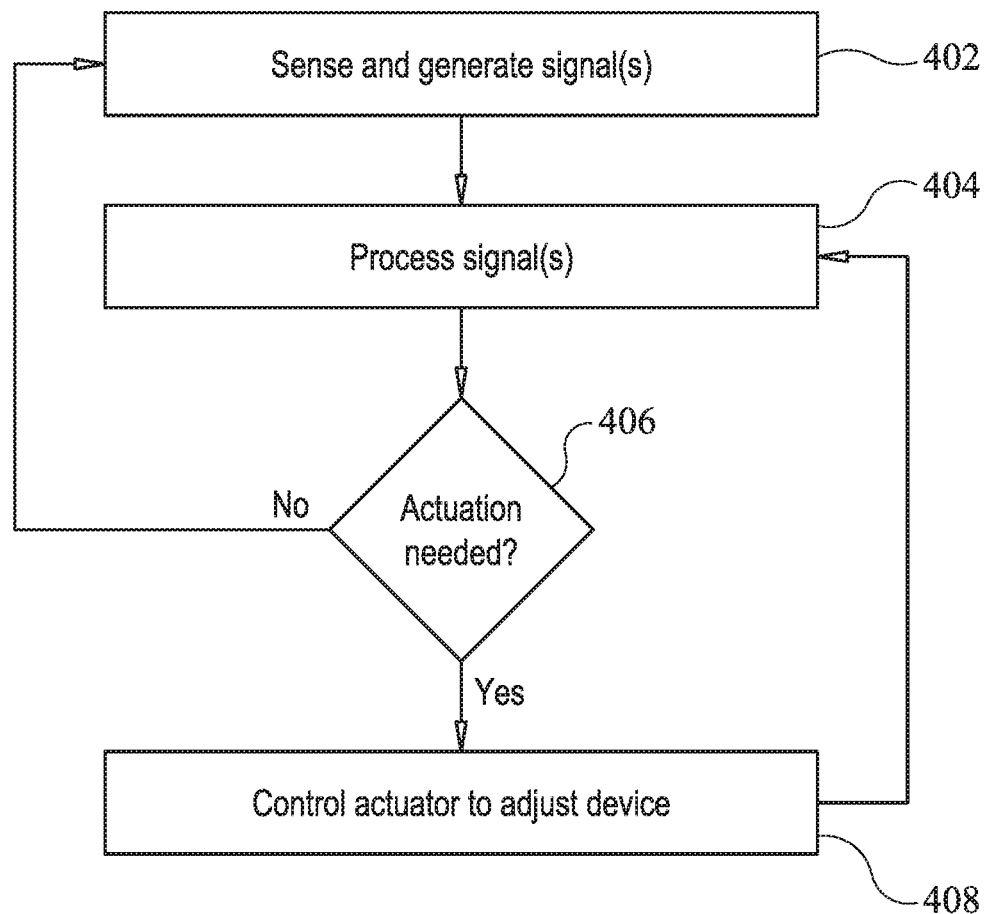
FIG. 4 is a flow chart illustrating a feedback loop included in processing by the system according to an embodiment of the present invention.

The actuator(s) 142 move(s) in direct proportion and response to the signals received from the actuator controller 128. A feedback sensor 144 sends a signal back to the actuator controller 128 indicating an amount of displacement of the actuator 142 (either relative or absolute) that has been achieved. FIG. 4 is a flow chart illustrating the feedback loop in greater detail. In a preferred embodiment actuator 142 comprises a bi-metallic actuator, in which two strips of different metals, which expand at different rates when heated, is used to convert a temperature change caused when actuator controller 128 inputs electricity to actuator 142, into mechanical displacement. One preferred pair of metals for making the bi-metallic actuator is aluminum and steel. Alternative pairs may be substituted, such as aluminum and invar (nickel-iron alloy); brass and invar; brass and steel (or iron), copper and invar; or copper and steel (or iron).

The different rates of expansion force the actuator 142 to bend one way if heated, and in the opposite direction if cooled below its initial temperature. Alternative embodiments of actuator 142 can be used, such as electromechanical, electromagnetic or hydraulic actuators. In the case of a hydraulic actuator, one or more balloons or other inflatable structures can be provided in actuator 142 and actuator controller 128 would include a pump and reservoir of fluid such as saline or the like.

Thus, the actuation subsystem applies force through the direct contact of the device 10 with the target tissue/organ 2 and may serve to mechanically reshape the tissue/organ 2 at levels determined by the controlling subsystem running an algorithm, based on the physiological/functional signals from the sensing module 110. The actuating subsystem 140 may also include a feedback sensor 144 that establishes a feedback loop to the controlling subsystem 120, thereby allowing for adaptive sensing and reshaping of the target tissue/organ 2 based on physiological and functional changes of that tissue/organ.

In FIG. 2, the need for actuation can be determined in direct response to the audio signals received form audio sensor 112 and/or in direct response to electrical signals received from electrical sensor 114. For example, electrical sensor 114 may directly detect voltage changes in the tissue itself in the form of analog signals that can be used for electrocardiogram (ECG) readings, in examples where the tissue/organ 2 being treated is the heart or portion thereof.

In the embodiment of FIG. 3, a motion sensor 116 is included in subsystem 110. The motion sensor(s) 116 can be used for organ/tissue 1 function detection (like described above with regard to the acoustic sensor 112 and electrical sensor 114, but wherein the signals in this case characterize the motion of the tissue/organ 2 detected) and/or for motion-driven electrical energy generation. Motion sensor 116 includes both energy conversion transducer 117 and inertial measurement component 118. For example, energy conversion transducer 117 may comprise piezo-electric transducer (s) (PET) and 2) inertial measurement component may comprise an accelerometer. The energy conversion transducer 117 translates kinetic energy received from the tissue/organ 2 (e.g., the pulsatile motion of the heart 3) into electrical energy in the form of electrical potential changes. The inertial measurement component 118 detects changes in acceleration of the target tissue/organ 2 and converts that to digital signals.

The electrical potential signals are sent from the motion sensor 116 to the energy conversion unit 132 in the controlling subsystem 120 where they are converted to electrical energy having requisite characteristics for charging the energy storage unit 126 (e.g., battery) from which the energy can be used to power the power supply 130, which also serves as the power source for the actuator(s) 142. A preferred embodiment of energy conversion transducer comprises a piezo-electric transducer (PET), which converts force/pressure or strain (relative motion) at the transducer membrane to electrical charge in the form of voltage changes. The PET acts as an AC voltage source. This voltage source induces current flow to 132, which converts AC to DC (via rectifier) and then stores that electrical energy within 126 and/or 132. Energy storage can be accomplished using a solid state (preferred) or chemical battery, and/or a super capacitor.

FIG. 4 is a flow chart illustrating a feedback loop carried out during operation of system 100 according to an embodiment of the present invention. At event 402, one or more different types of sensing (e.g., audio, electrical and/or motion) are performed by subsystem 110 in manners described above, and signals from the sensing(s) are sent to the controlling subsystem 120. Optionally, but not necessarily, energy conversion and storage can be carried out via motion sensor 116 and energy conversion unit as described above. The microprocessor 124 of the controlling subsystem 120 at event 404 processes the signals received using an algorithm to determine whether one or more of the signals are considered to represent normal functioning within a range of what is considered to be normal functioning according to data stored in data storage 122. If it is determined that the tissue/organ 2 is not normally functioning, the microprocessor at event 406 determines that actuation is needed and controls the actuator controller 128 to actuate the actuator at event 408 to adjust the device that the system 100 controls and which is in contact with the tissue/organ 2. The feedback sensor 144 then sends feedback signals to the control subsystem 120 which are received by the processor 124 to track how much the actuator was moved, in which direction. This information is used by the microprocessor 124 to keep track of how far the actuators can be moved and to match the position of the actuators with the results obtained. The sensing subsystem 110 continues to sense and generate signals. Thus, upon feedback at event 408, the control subsystem 404 processes the feedback signals and the current signals received from the sensing subsystem 110 to determine whether the actuators have been moved sufficiently to return the functioning to normal. If the functioning has not yet returned to normal (or the actuation has "overshot" normal, so that functioning now exceeds the opposite end of the range of normal functioning) as determined by processing at event 404 and determining whether actuation is needed at event 406, the control subsystem repeats event 408 and events 408, 404 and 406 continue to loop until normal functioning has been achieved.

Thus this closed loop feedback portion of the system 100 determines actuation required—more, less, or same displacement—by sensing changes in the acoustic, motion, and/or electrical signals. In an example involving treatment of the mitral valve, if the heart sounds from the mitral valve area indicate reduced mitral regurgitation, the controlling subsystem 120 will stabilize the displacement of the actuator 142. However, if the same or more mitral regurgitation is indicated through the heart sounds, the controlling subsystem 120 will either reduce or increase displacement of the actuator 142 until target reduction of mitral regurgitation is achieved.

Note that the sensing and generating at event 402 also continues so that real time, updated signals are used at each loop of event 404. When it is determined that actuation is no longer needed, as when functioning has been normalized, processing goes from event 406 to event 402 to continue sensing. Thus this closed-loop feedback portion of the system 100 determines actuation required—more, less, or same displacement—by sensing changes in the acoustic, motion, and/or electrical signals. In an example where mitral valve regurgitation is being treated, if the heart sounds from the mitral valve area indicate reduced mitral regurgitation to the "normal" range, the controlling subsystem 120 will stabilize the displacement of the actuator(s) 142. However, if the same or more mitral regurgitation is indicated through the heart sounds, the controlling subsystem 120 will either reduce or increase displacement of the actuator(s) 142 until target (predefined range of normal) reduction of regurgitation is achieved.

Figure 5:
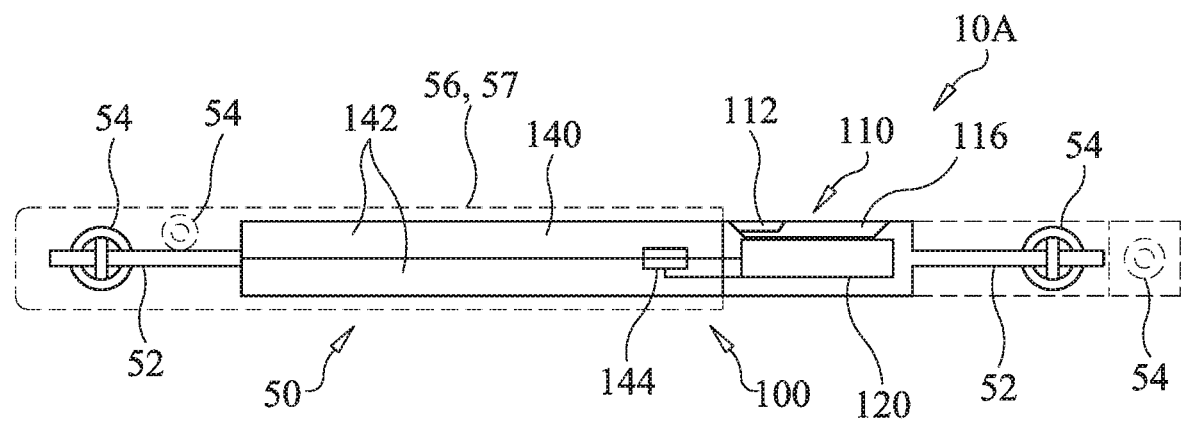
FIG. 5 illustrates an implantable device incorporating a system therein, according to an embodiment of the present invention.

FIG. 5 illustrates an implantable device 10A incorporating system 100 therein, according to an embodiment of the present invention. Device 10A is configured to be anchored to tissue/organ 2 of a patient so as to be operable to apply forces thereto to modify the functioning of the tissue/organ 2. For example, device 10A can be installed epicardially on the heart 3 of a patient. In one preferred embodiment, device 10A can be installed epicardially on the heart 3 over a target location to effect reshaping of the mitral valve annulus. In another use, device 10A can be configured to be installed epicardially on the heart 3 to apply forces thereto to improve tricuspid valve functioning.

Device 10A comprises a main body portion that is elongated and structured to include sensing subsystem 110, controlling subsystem 120 and actuating subsystem 140. The sensing system includes acoustic sensor 112 and motion sensor 116, both of which are positioned to interface with and directly contact the tissue/organ 2. Controlling subsystem 120 is located adjacent the sensing subsystem 110 in this embodiment, while actuating subsystem 140, includes bimetallic actuator 142 and feedback sensor 144, with actuator 142 extending over a majority of the length of the main body 50. Extension rods 52 may extend from both ends of main body 50 and be configured to engage with tissue anchors 54. Tissue anchors 54 may be selected from many variable types, including, but not limited to, any of those disclosed in US Patent Application Publication No. 2010/0010538 published on Jan. 14, 2010, which is hereby incorporated herein, in its entirety.

Main body 50 (excluding subsystem 110) and/or rods 52 may be surrounded by or encased within an outer covering 56. In some embodiments the outer covering 56 may be an atraumatic, bioabsorbable and/or biocompatible covering. For example, in some embodiments the outer covering 56 may be a compliant material, for example a polymeric over-mold, such as a silicone over-mold. In some embodiments, the outer covering 56 may include and/or be wrapped in a sheath 57, which may comprise an expanded polytetrafluoroethylene (ePTFE) material, a polyester knitted fabric, a polyester velour, a polypropylene felt, a woven or braided fabric, a non-woven fabric, porous material, or other textile material that is biocompatible. Further material choices for outer covering 56 and/or sheath 57 can be any of those described with regard to pad 58 in US Patent Application Publication No. 2010/0010538. The outer covering 56, which may be at least partially formed of a compliant material, may more evenly distribute stresses from the rod portions 52 to the surface of the tissue/organ, prevent lateral motion of the device 50 positioned on the tissue/organ, and/or provide an area for securing the device 50 to the tissue/organ. In some embodiments the outer covering 56 may distribute clamping forces to avoid occluding arteries and/or veins on the myocardium and/or epicardium or other tissue to which device 50 is attached. In some embodiments the outer covering 56 may provide sufficient torsional flexibility, allowing the device 50 to conform to the contours of the heart or other tissue/organ to which it is attached. When a sheath 57 is employed, sheath 57 may promote tissue in-growth into interstices of the sheath, and/or provide adequate frictional forces to hold the device 10B in contact with the heart and prevent migration of the device 10B once positioned on the heart.

Device 10A may be constructed of atraumatic and biocompatible materials that serve to encase the electronics and mechanical components and provide the underlying structure that establishes both apposition to the tissue/organ 2 and direction of actuation motion. The device materials as constructed, may be liquid impermeable and non-corrosive. The electronic components may be constructed with electronic potting or conformal coating to adequately protect the sensitive electrical components from the biological environment.

Rather than capturing the tissue anchors 54 with the rod extensions 52 as shown in solid lines in FIG. 5, the device could alternatively be anchored by installing tissue anchors 54 (shown in phantom lines) through the covering 56. Further alternatively, anchors 54 captured by rods 52 can be used in combination with anchors 54 installed through the covering 56. Further alternatively, tissue anchors 54 can be anchored in target tissue prior to installing the device and the rod extensions 54 can subsequently be attached to the implanted tissue anchors 54 so as to anchor the device. In any of these embodiments, anchors 54 can be electrically conductive and optionally electrically connected to control subsystem 120 to function as electrical sensors 114.

The extension shafts 52 may be formed of any desired materials, including those from which tissue anchors can be made, such as a metal, metal alloy, polymer, a metal-polymer composite, combinations thereof, and the like, or any other suitable material that is biocompatible. Some examples of suitable metals and metal alloys include stainless steel, such as 304V, 304L, and 316LV stainless steel; mild steel; titanium, nickel-titanium alloy such as linear-elastic and/or super-elastic nitinol; other nickel alloys such as nickel-chromium-molybdenum alloys, and the like. Extension shafts 52 may be welded, soldered or otherwise bonded, or integral with main body 50. In some embodiments the extension shafts 52 and main body 50 may be rigid, non-flexible. By rigid, what is meant is that the shafts 52 and main body 50 have sufficient rigidity to maintain a desired shape without deformation under normal operating conditions. Thus, application of a typical external force on the extension shafts 52 and or main body 50 will not appreciatively alter the shapes thereof, as the only change in shape desired is that that will be actuated by the actuator controller 128. For example, in some embodiments an external force of 5 Newtons or less, 10 Newtons or less, 15 Newtons or less, 20 Newtons or less, or 25 Newtons or less applied to the extension shafts 52 and/or main body 50 would not result in appreciable deflection, deformation or bending thereof. Furthermore, the extension shafts 52 and main body 50, unlike a cord or cable, may be capable of withstanding compressive forces without collapsing and/or may be capable of withstanding bending forces without deflection. In some embodiments, the extension shafts 52 and main body 50 may have moduli of rigidity of greater than 25 GPa, greater than 30 GPa, greater than 40 GPa, greater than 50 GPa, greater than 60 GPa, greater than 70 GPa, or greater than 80 GPa.

In some embodiments, the main body 50 and extension shafts 52 may be straight or substantially straight, or in other embodiments, the main body 50 and extension shafts 52 may be curved or bent into a desired shape. In some embodiments the main body 50 and extension shafts 52 may have a curvature approximating the curvature of the external curvature of a wall of a heart. In some embodiments, the extension shafts 52 may be eliminated altogether, such that the main body 50 extends over the lengths occupied by the extension shafts 52 in FIG. 5.

In some variants of this and all other embodiments described herein, the device may include a drug eluting coating in addition to or as an alternative to the outer covering 56. The drug eluting coating may perform a controlled release of a therapeutic agent over a specified period of time. The therapeutic agent may be any medicinal agent which may provide a desired effect. Suitable therapeutic agents include drugs, genetic materials, and biological materials. Some suitable therapeutic agents which may be loaded in the drug eluting coating include, but are not necessarily limited to, antibiotics, antimicrobials, antioxidants, anti-arrhythmics, cell growth factors, immunosuppressants such as tacrolimus, everolimus, and rapamycin (sirolimus), therapeutic antibodies, wound healing agents, therapeutic gene transfer constructs, peptides, proteins, extracellular matrix components, steroidal and non-steroidal anti-inflammatory agents, anti-proliferative agents such as steroids, vitamins and restenosis inhibiting drugs, such as TAXOL®, paclitaxel (i.e., paclitaxel, paclitaxel analogues, or paclitaxel derivatives, and mixtures thereof).

Figure 6:
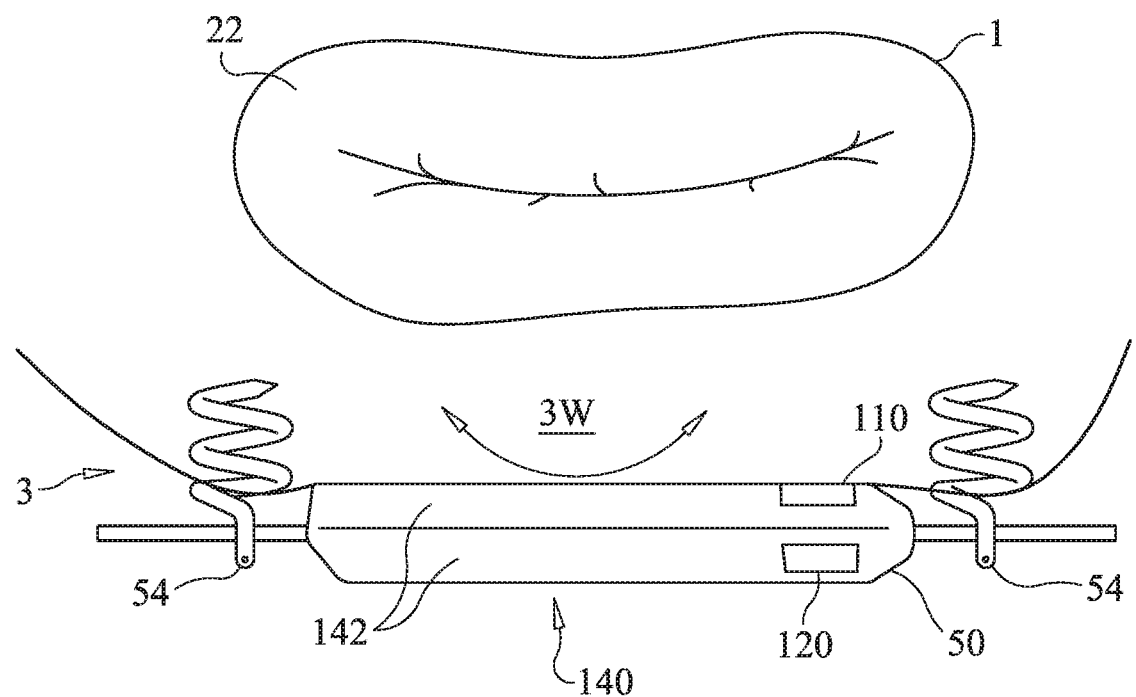
FIG. 6 illustrates the device of FIG. 5 having been epicardially attached, according to an embodiment of the present invention.

FIG. 6 illustrates one of the preferred embodiments for implantation of the device 50, wherein the device 50 is attached epicardially to the wall 3W of the heart 3 for treatment of the mitral valve 22 of the heart 3 to treat mitral regurgitation, for example. The device 50 may be anchored to the epicardial surface of the wall 3W of the heart 3 at the level of the mitral valve 22 via tissue anchors 54 as described. Actuation of the actuator 140 as described previously can be performed after anchoring the device 50, so that the ends of the actuator 140 can bend inwardly to apply additional force to the wall 3W of the heart 3 and therefor also to the mitral valve 22 to assist it in closing during diastole so as to decrease or eliminate mitral regurgitation. Alternatively, the actuator 142 can also be driven outwardly (as indicated by the bi-directional arrows in FIG. 6) so as to decrease the amount of force applied to the heart wall 3W and ultimately, the mitral valve annulus, if necessary.

Figure 7A:
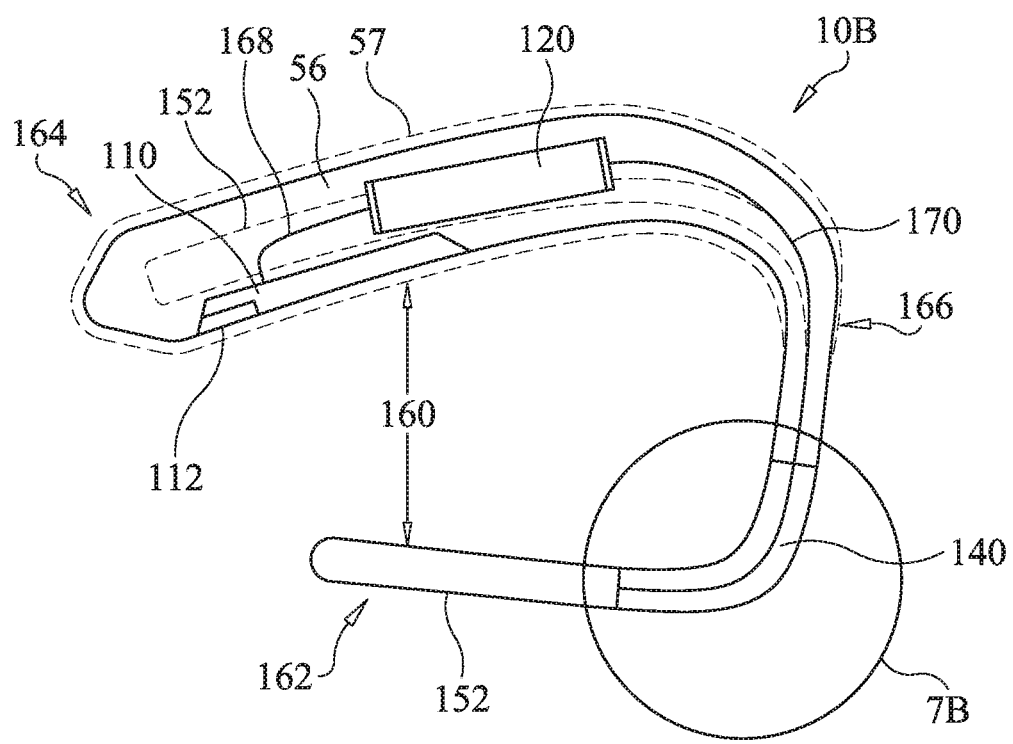
FIG. 7A illustrates an implantable device incorporating a system therein, according to another embodiment of the present invention.

FIG. 7A illustrates another preferred embodiment of a device 10B configured to be implanted for treatment of mitral regurgitation according to an embodiment of the present invention. In this embodiment, device 10B may have a generally U-shape or C-shape when viewed with this orientation. The device 10B may be shaped such that the distance 160 across the device 10B between the anterior segment 162 and the posterior segment 164 defines the space between which the mitral valve 22 and mitral valve annulus (as well as the heart walls apposite these features) will be located after implantation of the device 10B and may determine the final anterior-posterior diameter of the mitral valve annulus. The anterior segment 162 may be substantially straight, and thus capable of residing in the transverse sinus of the heart. The posterior segment 164 may be arcuate, corresponding to the convex curvature of the posterior left ventricular wall of the heart 3. The lateral segment 166 interconnects the anterior 162 and posterior 164 segments with a sufficient length to establish the appropriate distance 160 between the segments 162 and 164 for effectively applying force to the mitral valve annulus to cause a reduction or elimination of mitral valve regurgitation. The main body or frame of device 10B is non-flexible and is rigid to an extent wherein the conformation shown is not readily deformed and is not deformed by the forces applied to it by the beating heart when it is implanted. Accordingly, the distance 160 is not altered by application of forces from the beating heart to the device 10B.

The posterior segment 164 includes the sensing subsystem 110 and controlling subsystem 120 as shown. The sensing subsystem may include any combination of the sensors 112, 114, 116 described previously, but preferably includes at least acoustic sensor 112 and motion sensor 116, both of which are positioned to interface with and directly contact the tissue/organ such as the posterior surface of the left ventricle of the heart 3. Controlling subsystem 120 is located adjacent the sensing subsystem 110 in this embodiment, while actuating subsystem 140 is located along portions of the lateral segment 166 and anterior segment 162, as shown, so that actuation of the actuator 142 causes bending between the anterior 162 and lateral 166 segments thereby decreasing or increasing the distance 160. The sensing subsystem 110 is in electric communication with the controlling subsystem 120 via one or more wires 168 and a resistive heating wire 170 interconnects the controlling subsystem 120 and the actuating subsystem 140. The controlling subsystem and at least a portion of rod 152 may be encased in covering 56 which may be silicone, or any of the other materials described previously. Final implantation of the device 10B may be secured by tissue anchors 54 installed through the covering 56 and into the epicardium and optionally, the myocardium. Rod 152 may be made of titanium, or any of the other materials described previously for making extension rods 52.

Figure 7B:
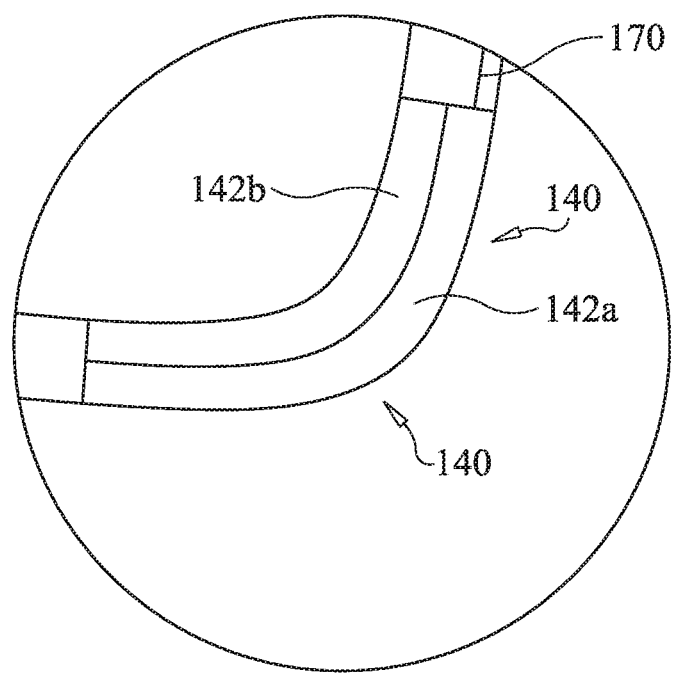
FIG. 7B is a detailed view of the portion of the device of FIG. 7A located within circle 7B.

FIG. 7B is a detailed view of the portion of device 10B located within circle 7B in FIG. 7A. Actuator 140 in this embodiment comprises a bi-metallic resistively heated actuator. A first metal component 142a of the actuator 142 is actively, resistively heated by application of electric current from controlling subsystem 120 via resistive heater lead (wire) 170. The other metal component 142b is passive and is not connected to the resistive heater lead 170. Thus, upon application of power through the lead 170, component 142a differentially heats up much greater than the amount by which component 142b heats up. This causes relatively more lengthening of the component 142a compared to the amount of lengthening of component 142b, resulting in bending the anterior segment 162 inwardly toward posterior segment 164 and therefore decreasing distance 160.

The lengths and orientations of the anterior 162, posterior 164 and lateral 166 segments may include any of those described in US Patent Application Publication No. 2012/0323314 which is hereby incorporated herein, in its entirety, by reference thereto. Device 10B may be configured so that the lateral segment 166 can be routed around the left lateral side of the heart, placing the anterior segment 162 in the transverse sinus and the posterior segment 164 on the posterior of the heart 3, such as on or inferior to the atrioventricular groove or in the oblique sinus of the heart. In some embodiments the lateral segment 166 may be routed around, over and/or under the left atrial appendage of the heart. In other embodiments, the lateral segment 166 may be routed over the left atrium of the heart.

Figure 8A:
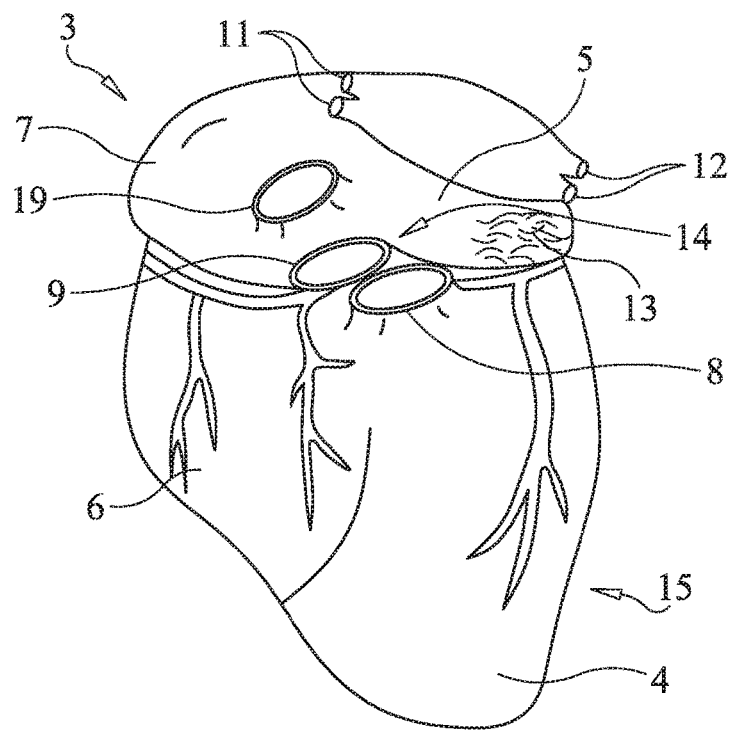
FIGS. 8A-8B are illustrations of a human heart, with the illustration in FIG. 8B viewed with the pericardium removed.
Figure 8B:
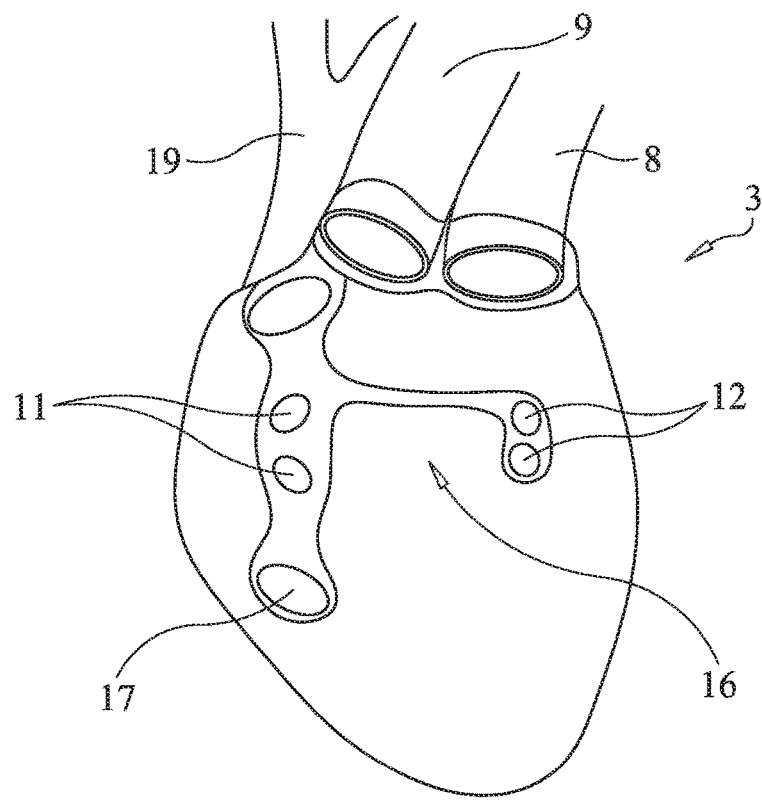

FIGS. 8A-8B are illustrations of a human heart 3, with the illustration in FIG. 8B viewed with the pericardium 15 removed. The chambers of the heart 3 include the left ventricle 4, the left atrium 5, the right ventricle 6, and the right atrium 7. Also shown are the pulmonary trunk 8, the aorta 9, the superior vena cava 19, the right pulmonary veins 11, the left pulmonary veins 12, and the left atrial appendage 13. The transverse sinus 14 is also referenced in FIG. 8A. The transverse sinus 14 is a pericardial cavity between the pericardium 15 and the epicardial surface of the heart 3 located posterior to the aorta 9 and the pulmonary trunk 8 and anterior to the left atrium 5 and the superior vena cava 19. The pericardial sac or pericardium 15, which is a tissue membrane covering the epicardial surface of the heart 3, is also shown removed from the heart 3 in FIG. 8B to further illustrate noteworthy anatomy of the heart 3. The oblique sinus 16 is a blind (e.g., cul-de-sac) recess on the posterior of the heart 3 formed between the pericardium 15 and the epicardial surface of the heart 3. The oblique sinus 16 lies generally between the right pulmonary veins 11 and the left pulmonary veins 12, with the thoracic part of the inferior vena cava 17 located on the side of the pulmonary veins 11. Only two layers of serous pericardium separate the transverse sinus 14 and the oblique sinus 16.

The devices described herein may be positioned on the epicardial surface of the heart 3 during a medical procedure. For example, in some embodiments the device 10 (referring to embodiments 10A, 10B and all other devices reference by 10 and a letter) may be installed on the heart 3 during a beating heart surgery, without the need of a heart/lung bypass machine. For instance, the device 10 may be implanted on the heart 3 through an open chest procedure (sternotomy) or a lateral thoracotomy. In some embodiments, the device 10 may be positioned on the heart 3 through a less-invasive endoscopic approach. For example, during a sternotomy, the thoracic cavity may be accessed for direct visual placement of the device 10 on the beating heart 3. Further alternatively the device may be implanted on the heart using minimally-invasive techniques with the use of ports or trocars installed in the chest of the patient to access the chest cavity under closed chest conditions. For any of these procedures, the pericardium 15 may be incised to access the pericardial cavity between the pericardium 15 and the epicardial surface of the heart 3. Upon accessing the pericardial cavity, the device 10 may be properly positioned on the epic ardial surface of the heart 3.

Figure 9A:
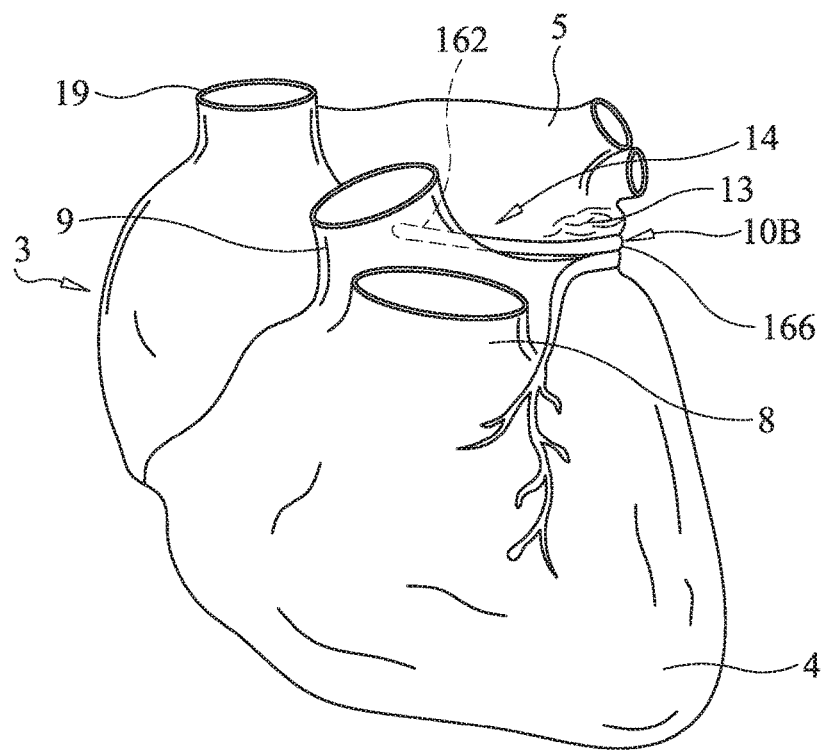
FIGS. 9A-9B illustrate locations of placement of a device epicardially on a heart according to an embodiment of the present invention.

For example, in the case of device 10B, FIG. 9A is an anterior view of the heart 3, with the device 10B placed on the epicardial surface of the heart 3. As shown in FIG. 9A, the anterior segment 162 of the device 10B is positioned in the transverse sinus 14 posterior to the aorta 9 and the pulmonary trunk 8 and anterior to the left atrium 5 and the superior vena cava 19. The lateral segment 166 may extend around the left lateral side of the heart 3 at a location inferior to the left atrial appendage 13. In other embodiments, the lateral segment 166 may extend around the left lateral side of the heart 3 at a location superior to the left atrial appendage 13 or over the left atrium 5.

Figure 9B:
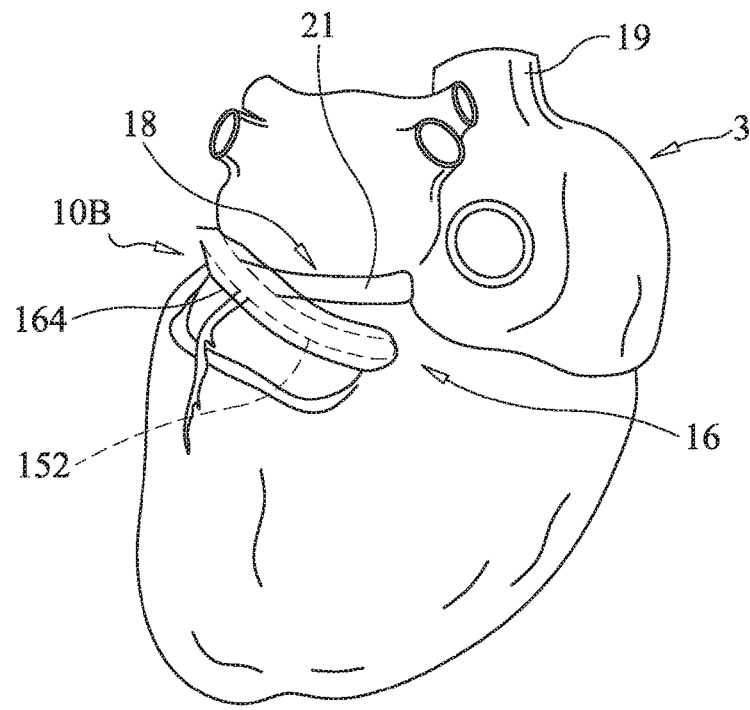

FIG. 9B is a posterior view of the heart 3 with the device 10B placed on the epicardial surface of the heart 3. As shown in FIG. 9B, the posterior segment 164 of device 10B is positioned on the posterior of the heart 3 inferior of the atrioventricular groove 18. The posterior segment 164 may be positioned such that it is just below the circumflex artery 21. In other embodiments, the posterior segment 164 may be positioned such that it is just above the circumflex artery 21.

Thus, the anterior segment 162 may be located in the transverse sinus 14. The posterior segment 164 may be positioned on the posterior side of the heart 3, such as on or inferior to the atrioventricular groove 18 or in the oblique sinus 16. In some embodiments, the posterior segment 164 may be positioned inferior to the atrioventricular groove 18 on the posterior side of the heart 3. The lateral segment 166 may extend around the left lateral side of the heart 3 such that the anterior segment 162 is properly positioned in the transverse sinus 14 while the posterior segment 164 is properly positioned on the posterior side of the heart 3, such as on or inferior to the atrioventricular groove 18 or in the oblique sinus 16. In some embodiments, the lateral segment 166 may extend around the heart 3 at a location inferior to the left atrial appendage 13. However, in other embodiments the lateral segment 166 may extend around the heart 3 at a location superior to the left atrial appendage 13 or over the left atrium 5 to join the anterior segment 162 and the posterior segment 164.

The devices 10 of the present invention, when properly positioned, may reside on the epicardial surface of the heart 3, interior of the pericardium 15. Thus, positioning of the device 10 may not require penetration of the heart into one or more of the chambers of the heart and/or may not require the device 10 to come into contact with blood being located inside the chambers of the heart 3. By placing the device 10 on the epicardial surface, exterior of the interior of the heart 3, complications associated with surgical procedures in which access is required to one or more of the chambers of the heart 3 are avoided. Furthermore, the time required to complete the surgical procedure may be greatly reduced from the time required for an open heart surgery or a surgical procedure requiring accessing the heart 3 through the vasculature.

The system 100 provided in device 10 in at least some embodiments is provided for self-adjustment of the device to enable it to autonomously adjust the distance between portions of the device. In some embodiments, the configuration of device 10 can be altered by operation of the actuator 140 in order to adjust forces applied to a heart 3 so as to alter the geometry of an annulus of the valve and thereby adjust the coaptation of the leaflets of the valve. Echocardiographic images may be taken during initial placement and anchoring of the device to determine initial settings of the actuator 40 and configuration of the device 10 to an optimal or desired position that minimizes or eliminates regurgitation through the valve. After completion of the surgical procedure the system 100 of the device 10 can continue to monitor as described, and adjust the configuration of the device 10, as needed to minimize or prevent regurgitation through the valve.

Figure 10:
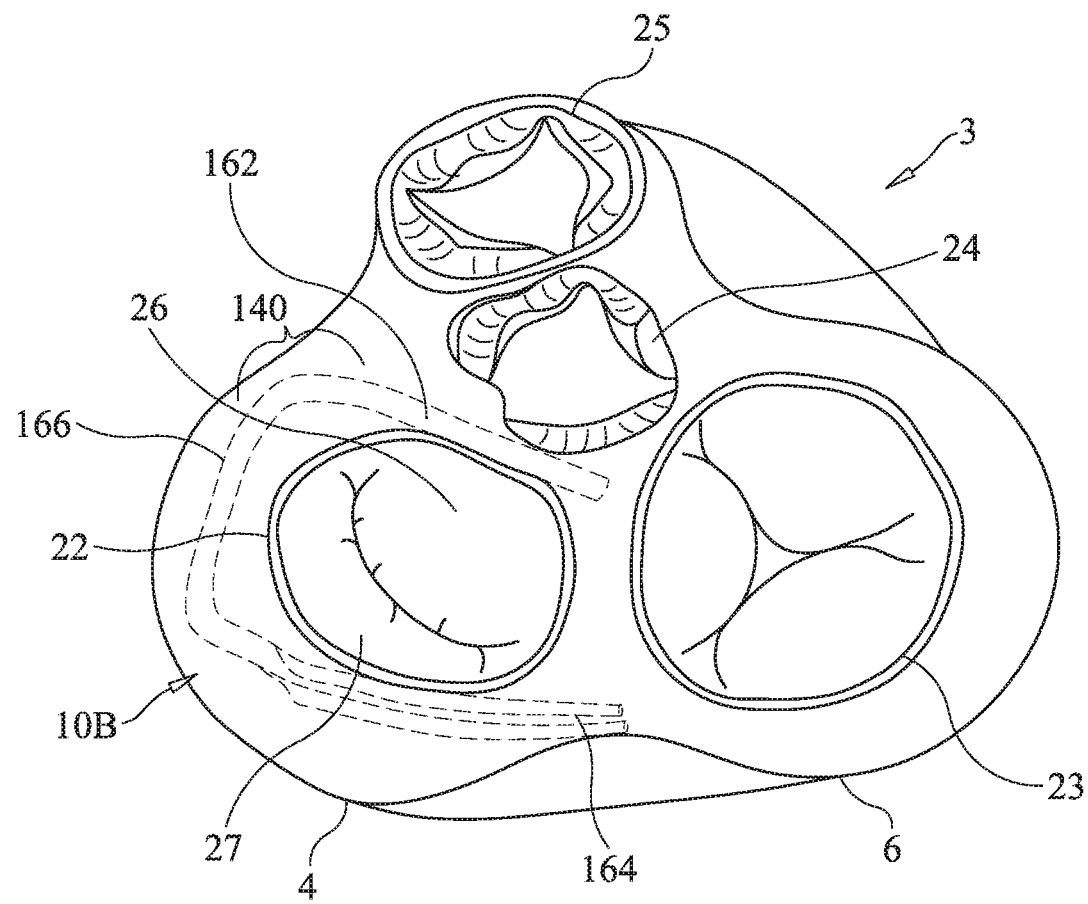
FIG. 10 is a top view of the ventricular portion of a heart, with the atria removed, and illustrating a device in phantom, according to an embodiment of the present invention.

For example, in device 10B, the distance between the anterior portion 162 and posterior portion 164 can be changed by operation of the system 100 to actuate actuator 140 in manners as described above. FIG. 10 is a top view of the ventricular portion of the heart 3 with the atria removed. With the atria removed, the mitral valve 22 between the left atrium 5 (not shown in FIG. 10) and the left ventricle 4 is clearly shown. Also shown is the tricuspid valve 23 between the right atrium (not shown in FIG. 10) and the right ventricle 6, as well as the aortic valve 24 leading to the aorta 9 and the pulmonary valve 25 leading to the pulmonary trunk 8. As shown in FIG. 10, the mitral valve 22 includes two leaflets, an anterior leaflet 26 and a posterior leaflet 27. The mitral valve 22 is shown closed as it would be during systole. The device 10B is shown in phantom (dashed lines) in FIG. 10 as the device 10B may not lie in the plane of the mitral valve 22 shown.

When device 10B is properly placed around the heart 3 as illustrated in FIG. 10, the shape of the device 10B may reduce the anterior-posterior measurement of the mitral valve 22. In other words, the device 10B may urge the posterior leaflet 27 of the mitral valve 22 and anterior leaflet 26 toward one another, providing better contact (coaptation) of the anterior 26 and posterior 27 valve leaflets of the mitral valve 22, which may reduce or eliminate mitral regurgitation. Device 10B is self-adjustable in ways already described above to alter the distance between the anterior segment 162 and posterior segment 164 through operation of system 100 to actuate actuating subsystem 140. For example, by actuating 140, anterior segment 162 and posterior segment 164 may be moved relatively closer together to further urge the leaflets 26 and 27 together. Alternatively, the actuation system 140 could be operated to increase the distance between anterior segment 162 and posterior segment 164 if needed, such as in a case where bringing the leaflets too close to one another could possibly worsen mitral regurgitation. Thus, the placement of device 10B as shown in FIG. 10 can be installed in a manner to initially reduce or eliminate mitral regurgitation. After completion of the implantation procedure, the device 10B is capable of monitoring for any changes in the state of the mitral valve 22 with regard to mitral regurgitation, and can alter the conformation of the device 10B via system 100 to change the forces applied to the heart 3 and mitral valve 22 to address situations in which mitral valve regurgitation is detected, so as to lessen or eliminate the mitral regurgitation or to return the mitral valve operation closer to the condition that existed upon completion of the implantation of the device 10B. Thus, the inclusion of the device 10B may allow the posterior leaflet 27 to more fully contact (coapt) the anterior leaflet 26 during systole to reduce or prevent retrograde blood flow through the mitral valve 22, thereby increasing the efficiency of the heart 3. During a medical procedure, echocardiographic images may be taken to determine the optimal or desired initial position and/or orientation of the device 10B to attain the proper anterior-posterior measurement (distance) and/or septal-lateral measurement (distance) of the annulus of the mitral valve 22 to minimize and/or eliminate mitral regurgitation. Details of electrocardiographic imaging, as well as measuring for septal-lateral distance, and also length of an anterior segment 162 to be used can be found in International Application Serial No. PCT/US2019/015300 titled "Epicardial Valve Repair System", which is hereby incorporated herein, in its entirety, by reference thereto.

Figure 11:
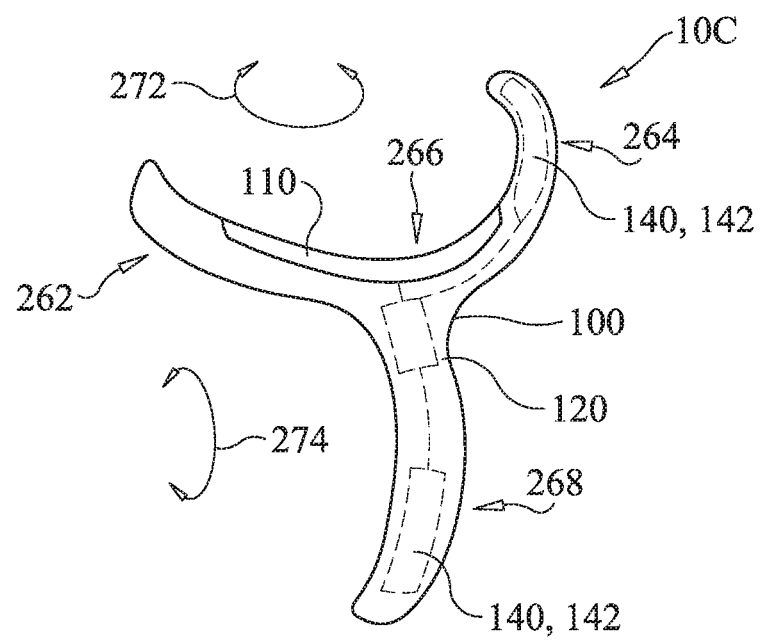
FIG. 11 illustrates an implantable device incorporating a system therein, according to another embodiment of the present invention.

FIG. 11 shows a device 10C according to another embodiment of the present invention. In this embodiment, device 10C includes anterior or first segment 262, posterior or second segment 264 and lateral or third segment 266 interconnecting the segments 262 and 264 similar to the configuration described with regard to device 10B. Additionally, an inferior or fourth segment 268 extends from the lateral segment 266 in a direction transverse to a direction along which the first, second and third segments 262, 264, 266 extend. As shown, segment 268 extends in a direction substantially normal to the direction in which at least one of anterior segment 262, posterior segment 264 and lateral segment 266 extend, but the angulation may vary between about sixty degrees and one hundred twenty degrees.

The structure of the device 10C that houses system 100 may be made of any of the same materials and components as described herein with regard to other embodiments, such as devices 10A and 10B, for example. The sensing subsystem 110 may be located along the lateral section 266 as shown, facing in a direction for sensing signals from the tissue/organ 2 to which the device is to be attached. Preferably, device 10C is configured for sensing data from the mitral valve 22, but, alternatively, an embodiment of this type could also be used for placement on the heart 3 for treatment of the tricuspid valve 23, in which case sensing subsystem would be used to sense signals from the tricuspid valve 23. Further alternatively, the sensing subsystem 110 may be positioned differently than shown, so as to be located in the posterior segment 264 or anterior segment 262, for example. A first actuating subsystem 140 may be located to extend between the lateral 266 and posterior 264 segments as shown, or alternatively, between the lateral 266 and anterior 262 segments. In either arrangement, the first actuating subsystem 140 is configured to be actuated to decrease and/or increase the distance between the anterior 262 and posterior 264 segments, similarly to what is described with regard to device 10B.

A second actuating subsystem 140 is located in the inferior or fourth segment 268 (but could alternatively extend within portions of segments 266 and 268) and is configured to be actuated to decrease and/or increase the distance between the inferior or forth segment 268 and the anterior and posterior segments 262, 264. The controlling subsystem 120 is shown located between the sensing subsystem 110 and second actuating subsystem 140 in FIG. 11, but need not be located there, as any location in which there is sufficient space with the device 10C and where subsystem 120 can be effectively electrically connected to the sensing subsystem 110 and first and second actuating subsystems 140 can be used for placement of the controlling subsystem 120. Accordingly, actuation of the first actuating subsystem 140 can be carried out to change the configuration of the device 10C in a first plane (indicated by arrows 272), and actuation of the second actuating subsystem 140 can be carried out to change the configuration of the device 10C in a second plane (indicated by arrows 274). The first and second planes may be normal to one another, but need not be and are not coplanar.

Figure 12:
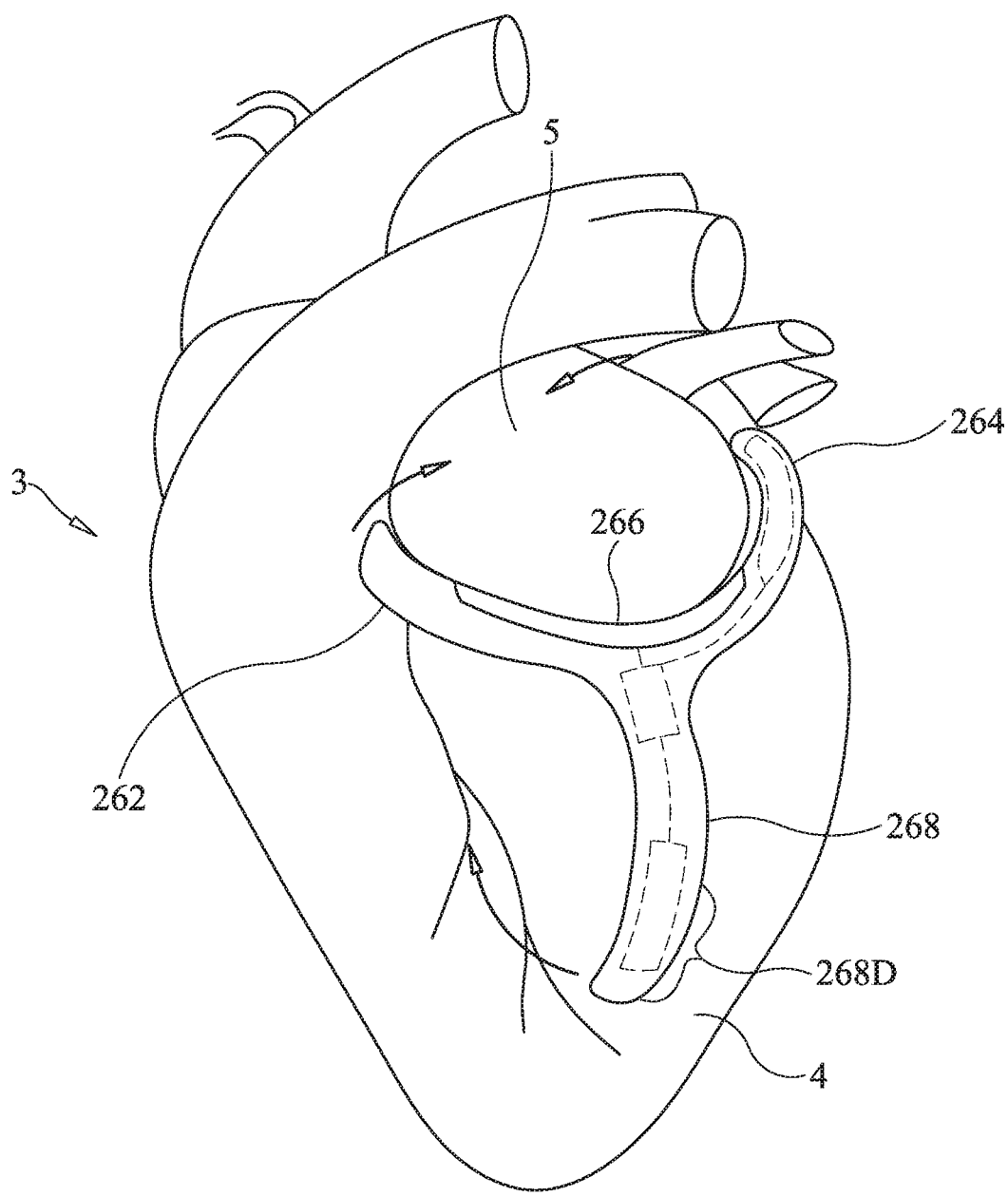
FIG. 12 illustrates an example of use of the device of FIG. 11 on a heart for treatment of mitral regurgitation, according to an embodiment of the present invention.

FIG. 12 illustrates an example of use of device 10C on a heart 3 for treatment of mitral valve regurgitation. The anterior, lateral and posterior segments 262, 266 and 264 are positioned epicardially on the heart 3 in an orientation permitting these segments to apply forces to the heart 3 that transfer to the mitral valve annulus and mitral valve 22, so as to reshape the same to reduce or eliminate mitral regurgitation, in manners already described above. In some embodiments, the anterior segment 262 may be substantially straight, and thus capable of residing in the transverse sinus 14 of the heart 3. In some embodiments, the posterior segment 264 may be arcuate, corresponding to the convex curvature of the posterior left ventricular wall of the heart 3. The lateral segment 266 interconnects the anterior 262 and posterior 264 segments with a sufficient length to establish the appropriate distance between the segments 262 and 264 for effectively applying force to the mitral valve annulus to cause a reduction or elimination of mitral valve regurgitation. Device 10C may be configured so that the lateral segment 266 can be routed around the left lateral side of the heart 3, placing the anterior segment 262 in the transverse sinus 14 and the posterior segment 264 on the posterior of the heart 3, such as on or inferior to the atrioventricular groove or in the oblique sinus of the heart 3. In some embodiments the lateral segment 266 may be routed around, over and/or under the left atrial appendage of the heart 3. In other embodiments, the lateral segment 266 may be routed over the left atrium 5 of the heart 3.

The inferior segment 268 extends inferiorly from the lateral segment 266 and is positioned along a portion of the length of the ventricle 4 as illustrated in FIG. 12, so a distal end portion 268D of the inferior segment 268 is positioned over an epicardial location of the ventricle 4 that is apposite to or inferior to one or more locations of insertion of chordae tendineae 28/papillary muscle 29 into the inner wall of the left ventricle 4.

Figure 13:
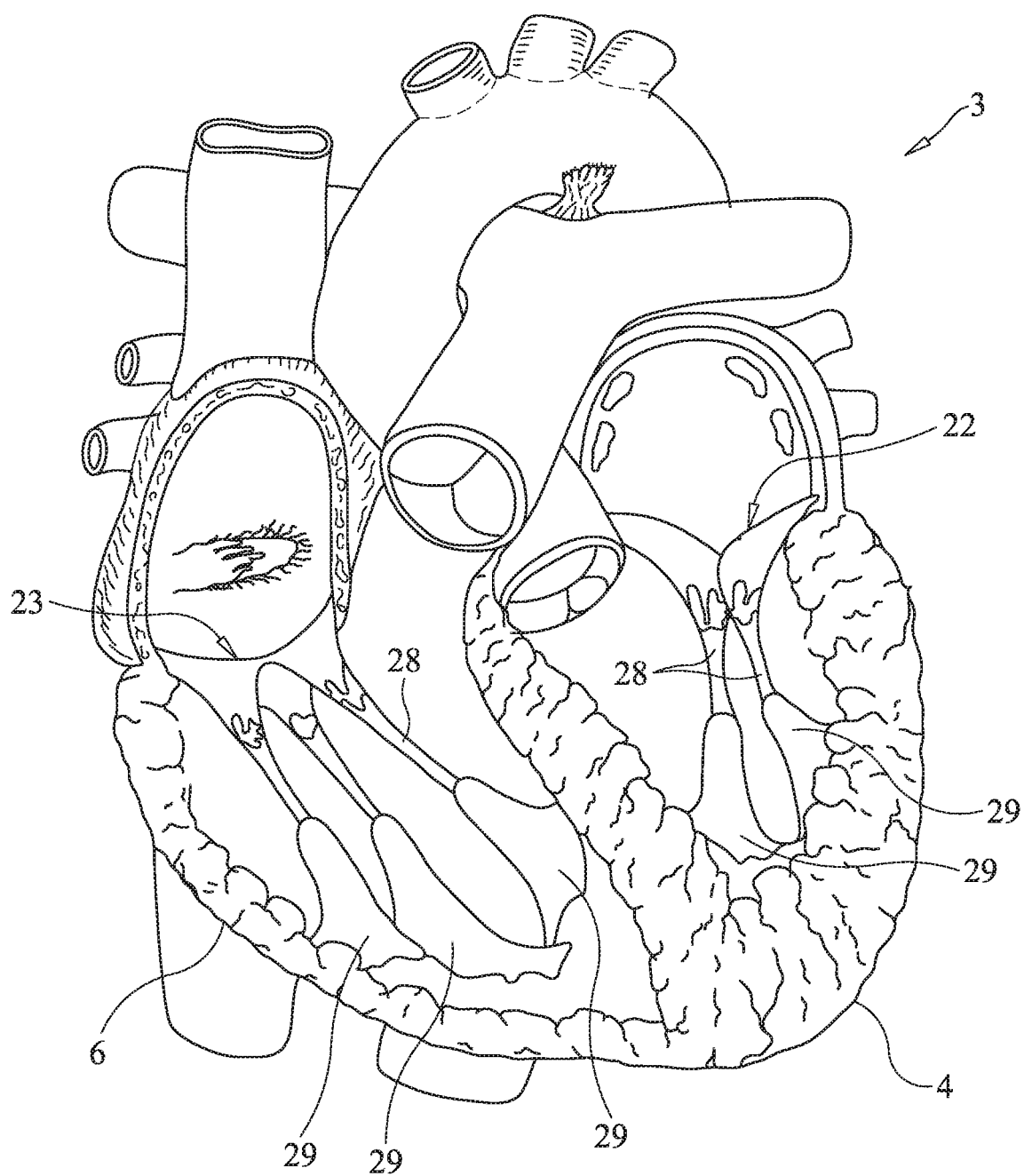
FIG. 13 is a cutaway view of a human heart illustrating chordae tendineae and papillary muscles in the left and right ventricles.
Figure 14:
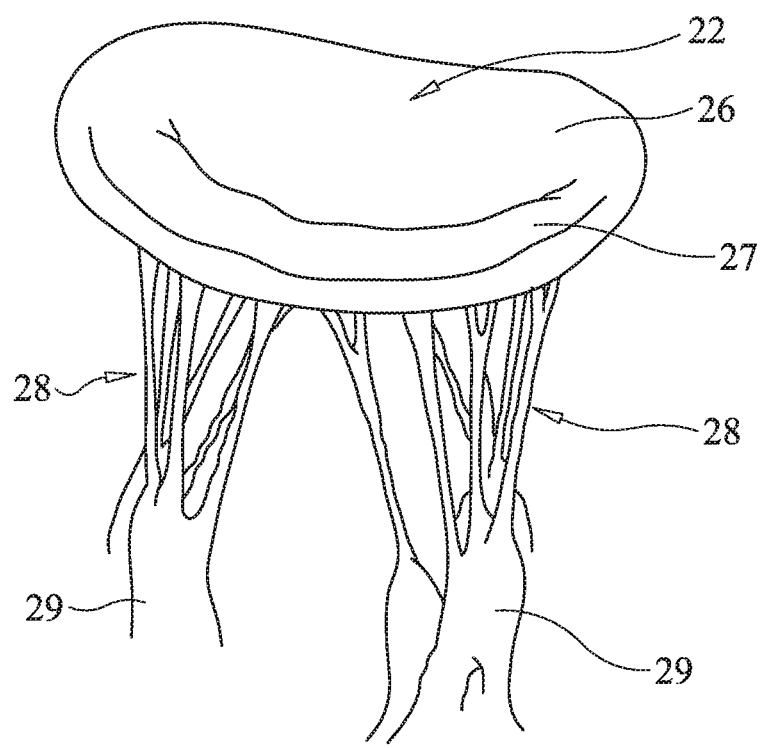
FIG. 14 is an isolated view showing attachment of the papillary muscles to the anterior leaflet and posterior leaflet of the mitral valve via chordae tendineae.

FIG. 13 is a cutaway view of a human heart 3 illustrating chordae tendineae 28 and papillary muscles 29 in the left 4 and right 6 ventricles. The papillary muscles 29 in the left ventricle 4 attach to the cusps of the mitral valve 22 and the papillary muscles 29 in the right ventricle 6 attach to the cusps of the tricuspid valve 23 via the chordae tendineae 28. FIG. 14 is an isolated view showing attachment of the papillary muscles 29 to the anterior leaflet 26 and posterior leaflet 27 of the mitral valve 22 via chordae tendineae 28. The papillary muscles 29 contract to prevent inversion or prolapse of the mitral valve leaflets 26, 27 (likewise, to prevent inversion or prolapse of the tricuspid valve leaflets by 29, 28 in the right ventricle) during systole (or ventricular contraction). The papillary muscles 29 of both the right 6 and left 4 ventricles begin to contract shortly before ventricular systole and maintain tension throughout. In the case of a normal heart 3 and heart valves, this prevents regurgitation, backward flow of ventricular blood into the atrial cavities, by bracing the atrioventricular valves against prolapse (prolapse described by being forced back into the atria by the high pressure in the ventricles).

However, in some cases of mitral and/or tricuspid regurgitation, the papillary muscles 29 and/or chordae tendineae 28 may apply too much contraction against the valve leaflets, either due to shortening of the chordae tendineae 28/papillary muscles 29 compared to normal or other reason. In these instances, reduction and/or prevention of regurgitation may be helped or accomplished reducing the amount of contraction or force applied through the chordae tendineae 28. For example, actuation of the second actuating subsystem 140 to move inferior segment 268 inwardly against the epicardial wall of the left ventricle 4 may cause a relative reduction in tension on the chordae tendineae 28, which, as a result will allow better closure of the mitral valve leaflets 26, 27 during systole, thereby reducing or eliminating mitral regurgitation. In combination with the reshaping accomplished by forces applied to the mitral valve annulus by the anterior and posterior segments 262, 264, the forces applied to the ventricle 4 to reduce tension on the chordae tendineae 28 may cooperate to reduce or eliminate mitral regurgitation. It is further noted that the device 10C could be adapted for similar functioning to reduce or eliminate tricuspid regurgitation from the right ventricle 6 through the tricuspid valve 23.

In the use case shown in FIG. 12, the actuators 142 of the first and second actuating subsystems 140 (see also FIG. 11) work in two areas: (1) around the annulus of the mitral valve 22; and (2) against the anterior chordae tendineae 28. By contracting around these two areas, compression of the anatomy is achieved. Around the mitral valve 22, the compression will serve to help close the mitral valve 22. In the area of the chordae tendineae 28, compression will serve to reduce tension on the chordae tendineae 28, which will in turn reduce the tendency toward opening of the mitral valve 22. Both mechanisms can serve to reduce mitral valve regurgitation.

Figure 15:
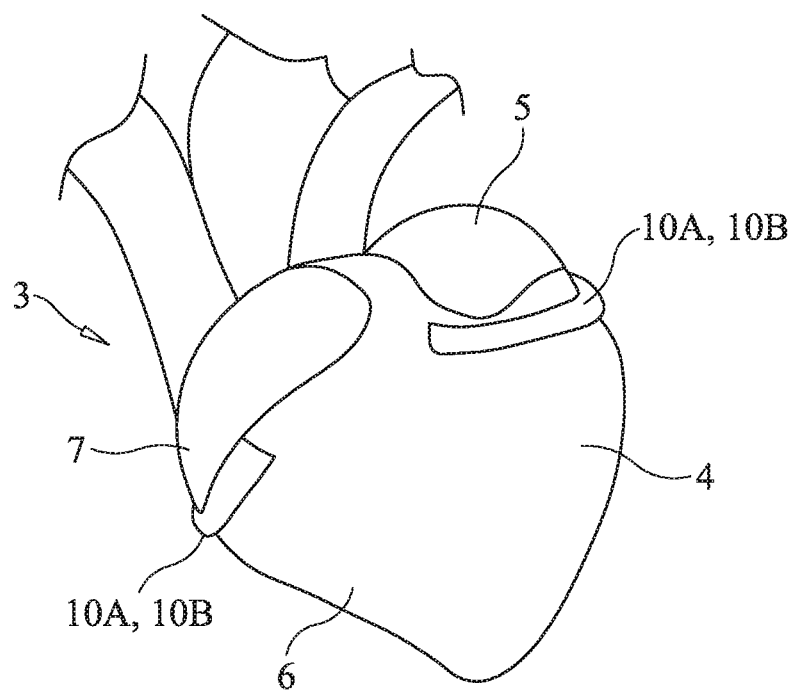
FIG. 15 illustrates various applications of devices of the present invention for use epicardially on the heart, according to embodiments of the present invention.

FIG. 15 illustrates various applications of the devices of the present invention for use epicardially on the heart 3. As already described, device 10A or 10B can be installed epicardially between the left ventricle 4 and left atrium 5 to treat mitral valve regurgitation. Additionally, or alternatively, device 10A or 10B can be configured for installation between the right ventricle 6 and right atrium 3 to treat tricuspid valve regurgitation.

Figure 16:
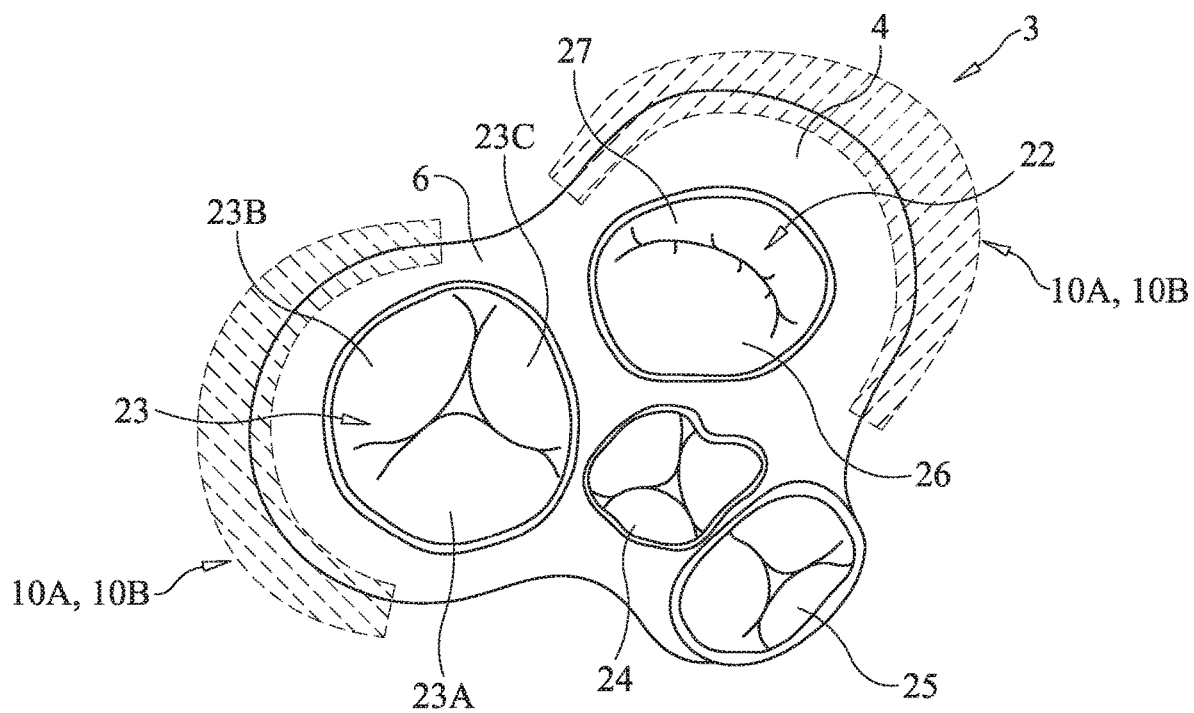
FIG. 16 is a top view of the heart of FIG. 15 with the atria removed and showing the devices of FIG. 15 in phantom.

FIG. 16 is a top view of the heart 3 of FIG. 15 with the atria removed. With the atria removed, the mitral valve 22 between the left atrium 5 (not shown in FIG. 15) and the left ventricle 4 is clearly shown and the tricuspid valve 23 between the right atrium 7 (not shown in FIG. 16) and the right ventricle 6 is clearly shown. Also shown are the aortic valve 24 leading to the aorta 9 and the pulmonary valve 25 leading to the pulmonary trunk 8. The mitral valve 22 is shown closed in FIG. 16 as it would be during systole. The device 10A, 10B is shown in phantom (dashed lines) in FIG. 16 as the device 10A, 10B may not lie in the plane of the mitral valve 22 shown. As shown in FIG. 16, the tricuspid valve 23 includes three leaflets 23A, 23B, 23C.

When device 10A, 10B is properly placed around the heart 3 as illustrated in FIG. 16, the shape of the device 10A, 10B may reduce the anterior-posterior measurement of the mitral valve 22. In other words, the device 10B may urge the posterior leaflet 27 of the mitral valve 22 and anterior leaflet 26 toward one another, providing better contact (coaptation) of the anterior 26 and posterior 27 valve leaflets of the mitral valve 22, which may reduce or eliminate mitral regurgitation. Device 10B is self-adjustable in ways already described above to alter the distance between the anterior segment 162 and posterior segment 164 through operation of system 100 to actuate actuating subsystem 140. For example, by actuating 140, anterior segment and posterior segment may be moved relatively closer together to further urge the leaflets 26 and 27 together. Alternatively, the actuation system 140 could be operated to increase the distance between anterior segment 162 and posterior segment 164 if needed, such as in a case where bringing the leaflets too close to one another could possible worsen mitral regurgitation. Thus, the placement of device 10A, 10B as shown in FIG. 16 can be installed in a manner to initially reduce or eliminate mitral regurgitation. After completion of the implantation procedure, the device 10A, 10B is capable of monitoring for any changes in the state of the mitral valve with regard to mitral regurgitation, and can alter the conformation of the device 10A, 10B via system 100 to change the forces applied to the heart 3 and mitral valve to address situations in which mitral valve regurgitation is detected, so as to lessen or eliminate the mitral regurgitation or to return the mitral valve operation closer to the condition that existed upon completion of the implantation of the device 10A, 10B. Thus, the inclusion of the device 10A, 10B may allow the posterior leaflet 27 to more fully contact the anterior leaflet 26 during systole to reduce or prevent retrograde blood flow through the mitral valve 22, thereby increasing the efficiency of the heart 3. During a medical procedure, echocardiographic images may be taken to determine the optimal or desired initial position and/or orientation of the device 10A, 10B to attain the proper anterior-posterior measurement (distance) and/or septal-lateral measurement (distance) of the annulus of the mitral valve 22 to minimize and/or eliminate mitral regurgitation.

When device 10A, 10B is properly placed around the heart 3 for treatment of the tricuspid valve 23 as illustrated in FIG. 16, the shape of the device 10A, 10B may reduce the anterior-posterior measurement and potentially, the lateral measurement of the tricuspid valve 23. In other words, the device 10A, 10B may urge the leaflets 23A, 23B, 23C inwardly toward the center of the tricuspid valve 23, and toward one another, providing better contact (coaptation) of the leaflets 23A, 23B, 23C, which may reduce or eliminate tricuspid valve regurgitation. Device 10A, 10B is self-adjustable in ways already described above through operation of system 100 to actuate actuating subsystem 140. For example, by actuating 140, anterior segment 162 and posterior segment 164 may be moved relatively closer together to further urge the leaflets 23A, 23B, 23C together. Alternatively, the actuation system 140 could be operated to increase the distance between anterior segment 162 and posterior segment 164 if needed, such as in a case where bringing the leaflets too close to one another could possibly worsen tricuspid regurgitation. Thus, the placement of device 10A, 10B as shown in FIG. 16 can be installed either for mitral valve treatment or tricuspid valve treatment, or for both, in a manner to initially reduce or eliminate mitral valve and/or tricuspid valve regurgitation. After completion of the implantation procedure, the device 10A, 10B is capable of monitoring for any changes in the state of the mitral valve or tricuspid valve with regard to mitral valve or tricuspid valve regurgitation, and can alter the conformation of the device 10A, 10B via system 100 to change the forces applied to the heart 3 and mitral valve and/or tricuspid valve to address situations in which mitral valve regurgitation or tricuspid valve regurgitation is detected, so as to lessen or eliminate the mitral valve and/or tricuspid valve regurgitation or to return the mitral valve or tricuspid valve operation closer to the condition that existed upon completion of the implantation of the device 10A, 10B. During a medical procedure, echocardiographic images may be taken to determine the optimal or desired initial position and/or orientation of the device 10A, 10B to attain the proper anterior-posterior measurement (distance) and/or septal-lateral measurement (distance) of the annulus of the mitral valve 22 and/or tricuspid valve 23 to minimize and/or eliminate regurgitation.

Figure 17:
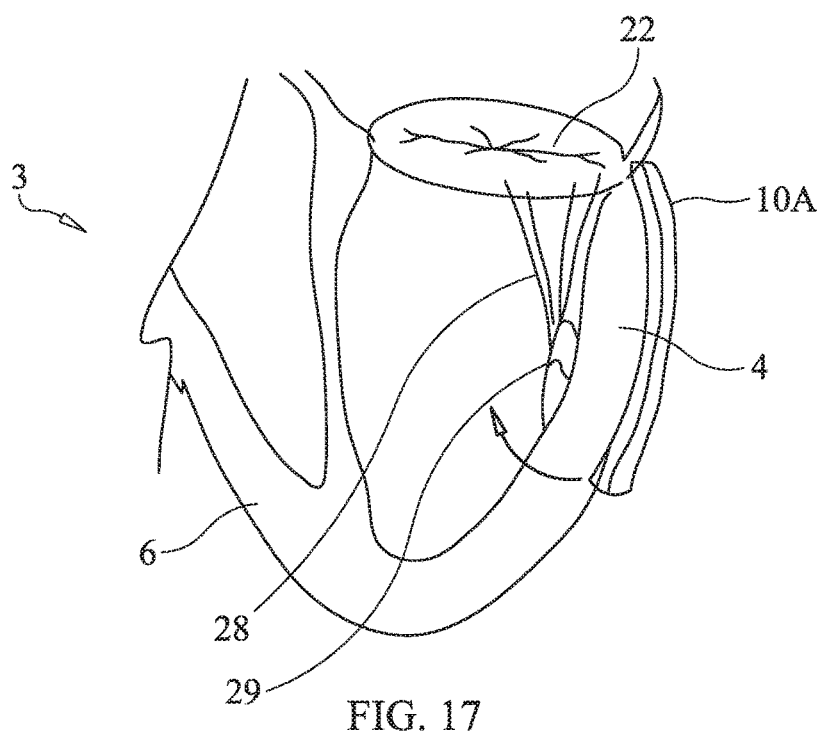
FIG. 17 is a partial, sectional view of a heart on which a device is epicardially installed for treatment of mitral valve regurgitation, according to an embodiment of the present invention.

FIG. 17 is a partial, sectional view of a heart 3 on which device 10A is epicardially installed for treatment of mitral valve regurgitation, according to an embodiment of the present invention. The device 10A when properly positioned, extends inferiorly from a location at or about the level of the mitral valve 22 and is positioned along a portion of the length of the ventricle 4, so that a distal end portion thereof is positioned over or inferior of an epicardial location of the ventricle 4 that is apposite to one or more locations of insertion of chordae tendineae 28/papillary muscle 29 into the inner wall of the ventricle 4. Actuation of the actuating subsystem 140 of device 10A/system 100 to move the distal end portion of device 10A inwardly against the epicardial wall of the left ventricle 4 in the direction shown by the arrow in FIG. 17 may cause a relative reduction in tension on the chordae tendineae 28, which, as a result will allow better closure of the mitral valve leaflets 26, 27 during systole, thereby reducing or eliminating mitral regurgitation.

Figure 18A:
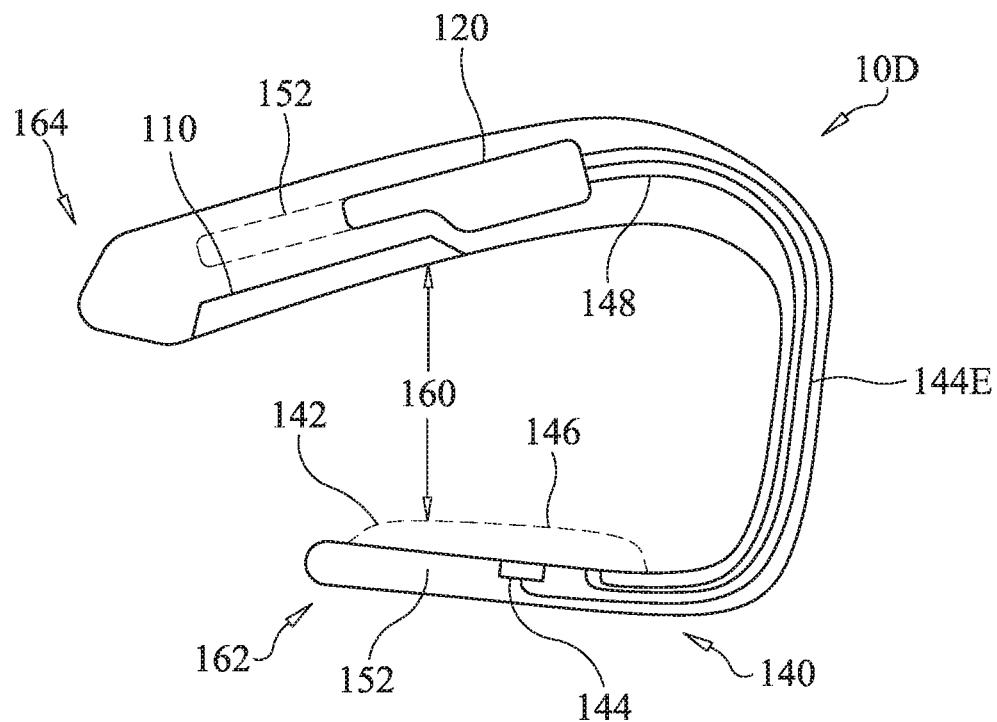
FIGS. 18A and 18B show variants of the embodiment of FIG. 7A.
Figure 18B:
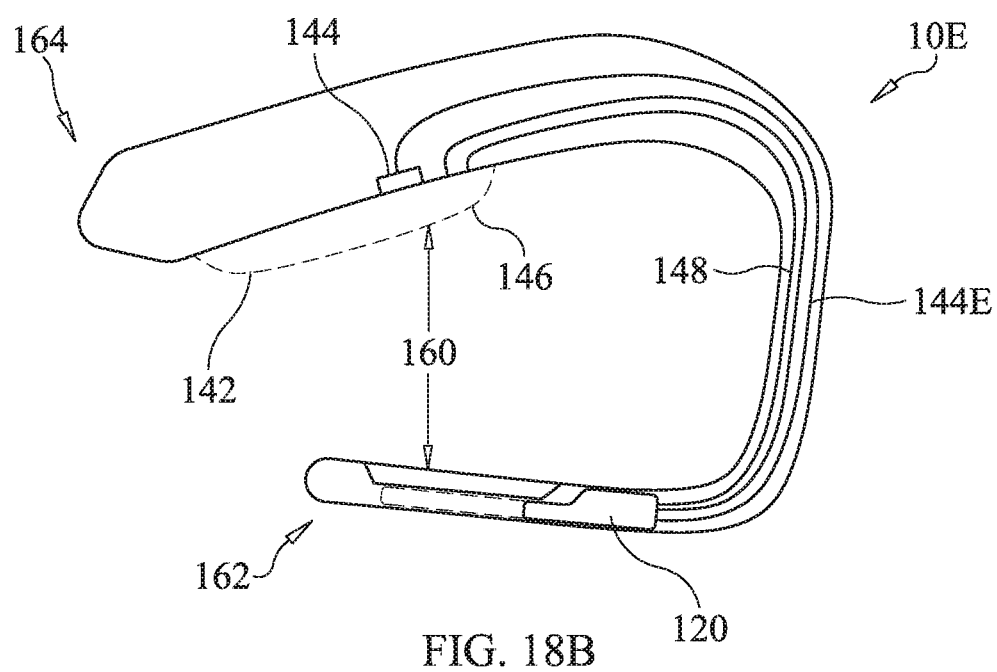

FIGS. 18A and 18B show variants of the embodiment 10B of FIG. 7A in which the variants are referred to as 10D in FIGS. 18A and 10D' in FIG. 18B. It is noted that the variant features of this embodiment, while applied to the embodiment of device 10B, could likewise be applied to the embodiments of 10A and 10C to form variants thereof, and that any of these variants can be used in all of the same manners as those described regarding devices 10A, 10B, 10C. While variations of features of device 10D and 10E as they pertain to device 10B are described here, it is noted that other features that are the same as those in device 10B are not repeated here. Devices 10D and 10D' utilize an expandable chamber 146 as the actuator 142 of actuating subsystem 140. In device 10D, the actuating subsystem 140 and expandable chamber 146 are located in the anterior segment 162, while in device 10D', the actuating subsystem 140 and expandable chamber 146 are located in the posterior segment 164, as the preferred embodiment of this variant. A conduit 148 connects the actuator controller in controlling subsystem 120 (located in posterior segment 164 in device 10D, while being located in the anterior segment 162 in device 10D') to deliver fluid (hydraulic or pneumatic) to or from the expandable chamber 146 and a reservoir (described further below). By expanding the expandable chamber 146, the system 100 can shorten the distance 160. Conversely, by removing fluid from the expandable chamber 146, the expandable chamber decreases in volume and the distance 160 lengthens as a result of the forces between 152 and the tissue that the expandable chamber 146 contacts. Feedback sensor 144 (in anterior segment 162 of device 10D; in posterior segment 164 of device 10D') is electrically connected to the controlling subsystem 120 by electrical lead 144E.

Figure 19:
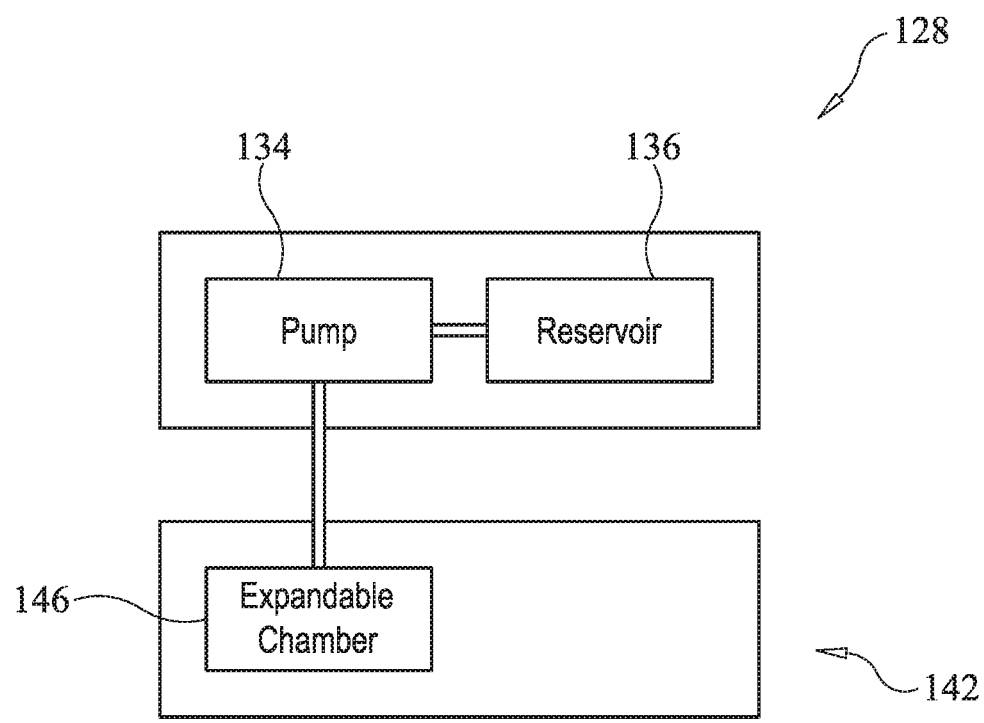
FIG. 19 schematically shows components for the control of the actuator of FIG. 18.

FIG. 19 schematically shows components for the control of the actuator 142 of FIG. 18, wherein some or all of these components can be contained in the actuator controller module 128 as shown, elsewhere in the controlling subsystem 100, elsewhere in the device 10D, or even external to the device 10D. The actuator controller module 128 is in electrical communication with the microprocessor 124 (which is also in electrical communication with the feedback sensor 144 and sensing subsystem 110 as described above) to control a pump 134 that is in fluid communication with reservoir 136 and expandable chamber 146, as illustrated. Reservoir 136 contains fluid to be used in expanding the expandable chamber 146 and also serves as a repository for fluid withdrawn from the expandable chamber. The fluid is preferably hydraulic, such as saline or other biocompatible fluid, but could alternatively be pneumatic (gas), although this is not preferred.

Figure 20A:
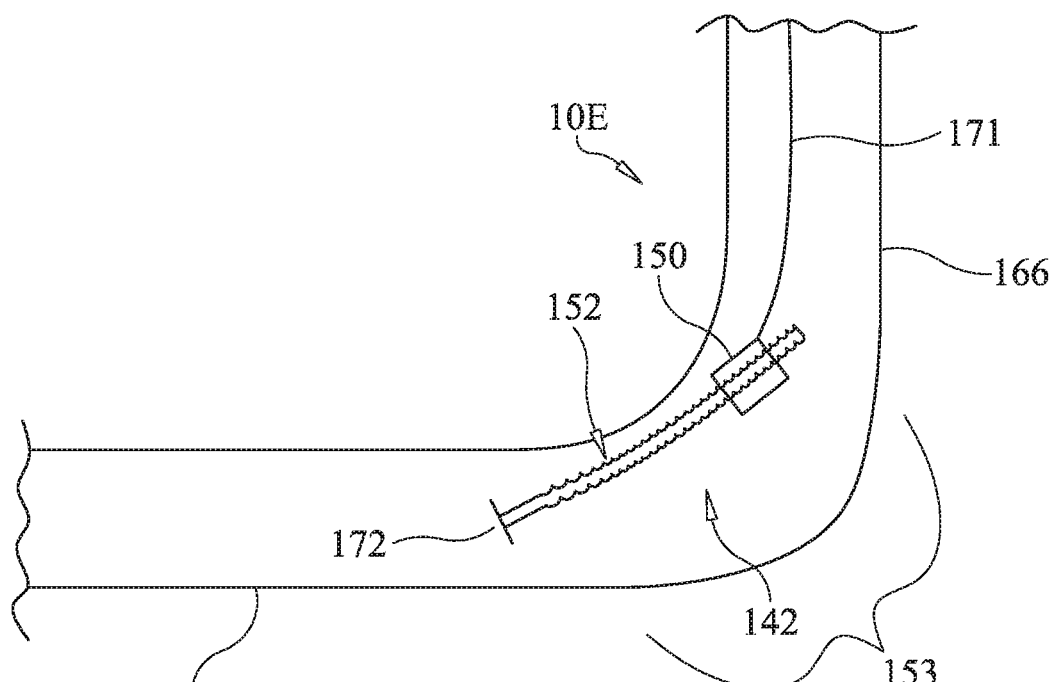
FIG. 20A shows a variant of the embodiment of FIG. 7B.

FIG. 20A shows a variant of the embodiment 10B of FIG. 7B in which the variant is referred to as 10E in FIG. 20. It is noted that the variant features of this embodiment, while applied to the embodiment of device 10B, could likewise be applied to the embodiments of 10A and 10C to form variants thereof and that any of these variants can be used in all of the same manners as those described regarding devices 10A, 10B, 10C. While variations of features of device 10E as they pertain to device 10B are described here, it is noted that other features that are the same as those in device 10B are not repeated here. Device 10E utilizes an electric motor 150 and drive train 152 as the actuator 142 of actuating subsystem 140. Motor 150 is electrically controllable by actuator controller 128 by one or more electrical leads 171. Motor 150 may be fixed relative to the device 10E. In FIG. 20, the drive train 152 includes a screw drive 152, although other mechanical equivalents could be substituted, such as chain drive, belt drive or other type of drive train, as would be apparent to one of ordinary skill in the art. In FIG. 20, the screw drive 152 is mounted at a distal end thereof to the device 10E in a manner that prevents its translation but allows its rotation. At the proximal end portion, the drive train 152 is engaged by the motor 150. The operation of the motor 150 can shorten or lengthen the distance between where the motor is mounted and where the distal end of the drive train is mounted at 172, as mount 172 includes mating threads that mate with the threads of the screw drive 152. Alternatively, the motor 150 can be mounted toward the distal end of the drive train and the proximal end of the drive train can be mounted to the device 10E to prevent translation thereof but allow rotation. By shortening the distance between the motor 150 and location 172, the system 100 can shorten the distance 160. Conversely, by lengthening the distance between the motor 150 and the location 172, the system 100 can lengthen distance 160. The portion 153 between the lateral segment 166 and anterior 162 and/or posterior 164 segment of the device 10E (arrangement 150, 152, 172 can be installed to operate between 162 and 166 or between 162 and 164, or both) is flexible so as to operate as a living hinge between the segments when the motor 150 is operated as described.

Figure 20B:
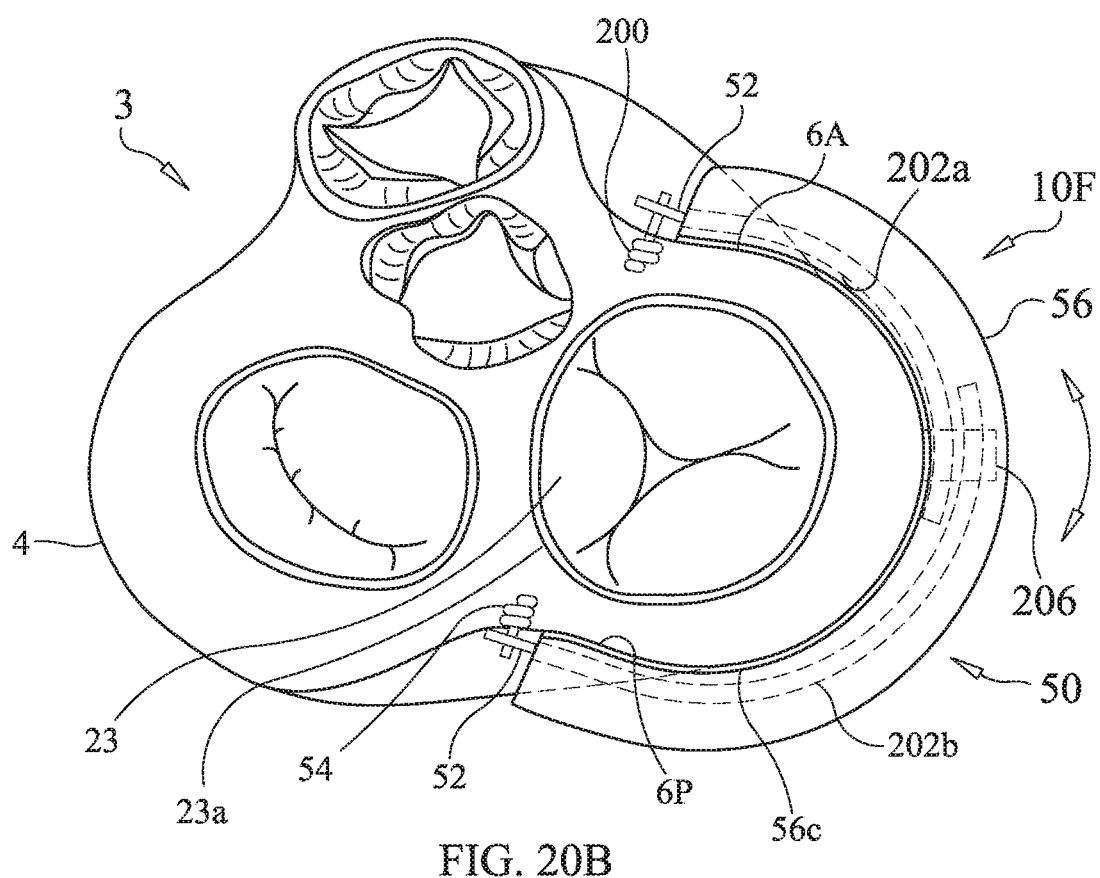
FIG. 20B illustrates a device having been installed epicardially on a heart of a patient for treatment of tricuspid valve regurgitation, according to an embodiment of the present invention.

FIG. 20B illustrates a device 10F having been installed epicardially on a heart of a patient for treatment of tricuspid valve regurgitation, according to an embodiment of the present invention. A measurement between the anterior and posterior locations 6A and 6P of the right ventricle can optionally be made, during visualization of the tricuspid valve 23 to watch for regurgitation amounts occurring under various force and deformation levels, so as to identify an optimum distance between the contact surfaces 56c of the device that will be applied to the locations where the measurement was taken. Alternatively the device 10F can be installed without taking the preliminary measurement and the device 10F can then be adjusted under visualization to reduce and/or eliminate tricuspid valve regurgitation. This adjustment after implantation can be performed whether or not the preliminary measurement has been taken. Device 10F is attached epicardially, in or about the plane of the tricuspid valve 23, as illustrated in FIG. 20B. FIG. 20B illustrates device 10F having been installed epicardially on the heart 3 of a patient for treatment of tricuspid valve regurgitation as one of the preferred embodiments of location of implantation. In this preferred embodiment, device 10F can be installed epicardially on the heart 3 over a target location to effect reshaping of the tricuspid valve annulus 23a. Preferably, the contact pad 56 of the device is as long as can be fitted to the heart 3 at this location, so that the contact surface 56C of the pad contacts the heart wall around as much of the tricuspid valve annulus 23a as possible. FIG. 20B shows that the pad 56 of the device 10F surrounds greater than 50% of the annulus 23a and can apply forces to as much of the epicardial surface surrounding the tricuspid annulus as possible. Preferably the pad 56 extends as far as is physically possible before it is prevented by heart structures from extending any further. Thus, the pad may surround a percentage of the annulus in a range from 30% to 70%, preferably 40% to 70%, more preferably 50% to 70%, even more preferably 60% to 70%. The device 10F may be anchored to the wall of the heart 3 at the level of the tricuspid valve 23 via tissue anchors in a manner as described with regard to previous embodiments.

Rod/rib 202 is provided in two parts, a first part 202a and a second part 202b that extend through the main body 50 of device 10F and form extension rods 52 that extend from both ends of main body 50. Rod/rib portions 202a, 202b are preferably substantially curved as shown, with a curvature configured to conform to the curvature of the epicardial walls of the right atrium 6 at the level of the tricuspid valve 23 as described. The main body is formed by pad 56 which surrounds or encases the portion of the rod/ribs 202a, 202b extending therethrough. As shown, the portions 202a, 202b are about equal in length, but this need not be the case. In FIG. 20B, the portions 202a, 202b are joined together by an actuator 206, which may be a gearbox, one-way ratchet mechanism, one or more screw drive mechanisms 172, 152, 150 or other mechanical component that allows the portions 202a, 202b to be driven therethrough in at least one direction. By driving the portions 202a, 202b through actuator 206, this effectively decreases or increases the distance between the contact surfaces 56C contacting the anterior and posterior walls 6A and 6P of the heart 3 on opposite sides of the tricuspid valve 23 as illustrated in FIG. 20B. For example, by relatively driving the portions 202a, 202b so that 202b moves upward through the actuator 206 and/or 202a moves downward through the actuator 206 in FIG. 20B, this causes the distance between contact at 6A and 6P to be reduced, thereby increasing the force and deformation on the walls of the heart 3 and on annulus 23a. Of course, movement in the opposite directions would have the opposite effect of reducing the force and decreasing the deformation. Actuator 206 may adjusted via control signals sent to the actuator 202 in any of the manners described herein with regard to actuator 142 or actuation subsystem 140. Actuator 206 may be a motorized gearbox, with battery power, for example, which could be actuated either directly by an actuation switch on the device 10F, or via wired or wireless actuation from a control subsystem 120. Further optionally, a manual controller could be provided for overriding automatic actuation when a surgeon or other user wants to move the actuator by directly controlling it. The motorized actuator 206 can be actuated to either increase or decrease the forces/deformation applied by the device 10F to the heart 3.

Figure 21:
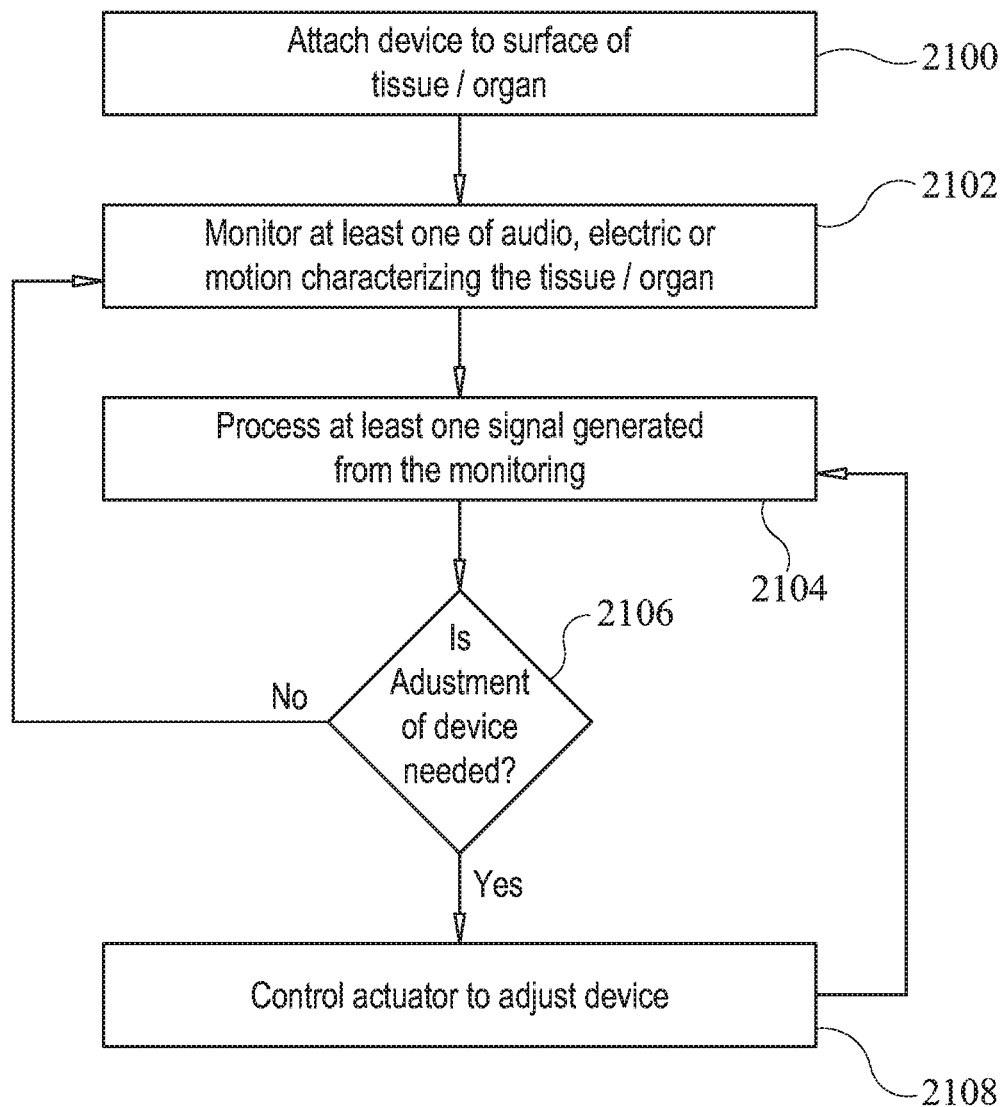
FIG. 21 illustrates events that may carried out in a method of using a device according to an embodiment of the present invention.

FIG. 21 illustrates events that may be carried out in a method of using a device 10 according to an embodiment of the present invention. At event 2100 device 10 is attached to the surface of a tissue or organ to be treated. Prior to implantation/attachment to the tissue/organ, the system 100 may be pre-energized, initialized, identified, and the device is sterilized. The device 10 is then placed on the target tissue/organ via either open surgery or minimally invasively (e.g. through ports via small incisions). Placement is guided either through direct visualization, endoscopic visualization, or indirect means such as radiographically. Once placed, the device 10 may be self-operating, powered, and actuated. Communication with the device 10 can be enabled through a transcutaneous lead or wirelessly via radio frequencies.

The tissue or organ may be any of those described above. In one preferred embodiment, device 10 is attached to the heart to treat mitral valve regurgitation. Among a number of different embodiments of treatment of mitral valve regurgitation, one preferred embodiment involves attaching device 10B to the heart 3 in the location and under the conditions already specified above. Radiographic or echogenic monitoring may be performed during event 2100 to verify that the device 10 has been properly installed, in the right location and with the correct configuration/force applied to the tissue/organ to effect satisfactory treatment, such as, but not limited to, significant reduction or abatement of mitral valve regurgitation.

Once the device has been successfully installed as well as after completion of the installation procedure, at event 2102, monitoring of at least one of audio, electric or motion of the tissue is performed via at least one sensor, which may be a sensor integrated into the device, a sensor that is part of the system but is provided externally of the device, or a sensor from another device or sensing unit that is not part of the system, but which the controlling subsystem of the system is configured to receive input from. The sensor may interface with the tissue/organ as already described previously. Alternatively, the sensor may monitor at a distance from the interface between the device and the tissue. At event 2104, the controlling subsystem 120 processes at least one signal received from the at least one sensor of the sensing subsystem 110 (and/or sensor 110' that is not part of the system) using an algorithm to determine whether the functioning of the tissue/organ has deviated significantly from normal so as to require adjustment of the device. At event 2106, if the controlling system determines that no adjustment is needed at this time, processing returns to event 2102. Alternatively, when it is determined at event 2106 that adjustment of the device 10 is needed at this time, then the controlling subsystem 120 via actuator controller 128 controls actuation of the actuator 142 to change the conformation of the device 10 so as to apply different forces to the tissue/organ where it makes contact. Processing then returns to event 2102, as continual monitoring may be carried out. At event 2104 the controlling subsystem also processes the changes in conformation of the device 10 carried out at event 2108 as received from the feedback sensor 144, so that this is taken into account along with the current sensing signal(s) that are processed.

In one preferred embodiment of epicardial treatment of mitral regurgitation associated with the mitral valve of a heart, anterior segment 162 of device 10B is positioned in the transverse sinus of the heart, and the posterior segment 164 is positioned on or inferior to the atrioventricular groove of the heart, where it is confirmed by imaging that the device 10B reshapes the annulus of the mitral valve sufficiently to significantly reduce or eliminate mitral valve regurgitation.

The anterior and posterior ends of device 10B at this time are spaced apart from one another by a predetermined distance and remain separated by a gap or opening after completion of this procedure.

In cases where the monitoring, processing and determining events result in a conclusion that adjustment of device 10B is needed, the controlling subsystem 120 actuates the actuator 142 of the actuating subsystem to reconfigure the device 10B so that the anterior and posterior ends of the device are spaced apart by a modified distance different from predetermined distance defined at the end of installation of the device 10B. The monitoring, processing, determining and actuating events can be carried out in real time by the system 100.

Figure 22A:
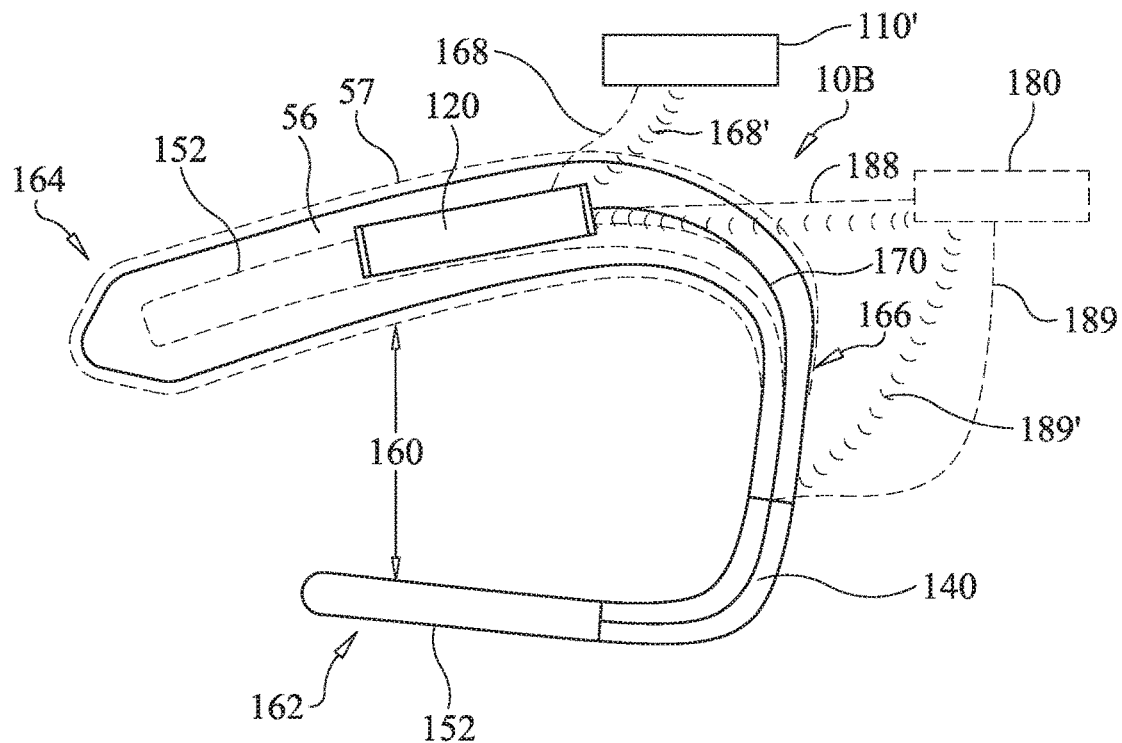
FIG. 22A illustrates a variation according to an embodiment of the present invention.

As noted above, a system according to the present invention may be provided in a single integrated system or a system having one or more separate modules. For example, a device 10 as described above includes sensing, controlling and actuating subsystems all integrated into the device. Alternatively, a device 10 could be provided with only controlling and actuating subsystems as integral to the device, while the sensing subsystem could be provided and implanted separately from the device and configured to communicate with the device, either by wired or wireless connection. FIG. 22A schematically illustrates such a variation, wherein device 10B' includes controlling subsystem 120 and actuating subsystem 140, while a sensing device 110' is provided separately of the device 10B' and is configured to input to controlling subsystem 120 in the same manner as described above for embodiments where the sensing subsystem is integrated in the device, wherein the input may be provided by wired 168 communication or wireless 168' communication. The sensing device 110' may be a sensing subsystem 110 and provided as part of the system and/or a sensing unit that is provided separately from the system, such as a sensor of another device, wherein the controlling subsystem 120 is configured to receive input from the other device, as sensing input. The other device may have been implanted prior to the implantation of device 10B' or could be implanted in the same procedure or even subsequent to implantation of the device 10B'. Optionally an external signal generator 180 may be provided for use by a user outside of the body of the patient that the device 10B' (or any other device 10 described herein) is implanted in. External signal generator 180 can be configured to provide control signals either to the control subsystem 120 or to the actuation subsystem 140 to actuate the actuator for manual adjustment of the device 10B', either by wired (188 or 189) or wireless (188' or 189') communication. This option can be provided to any embodiment of device described herein, regardless of whether sensing subsystem 110 is integrated or external, and regardless of whether control subsystem 120 is integrated or external.

Figure 22B:
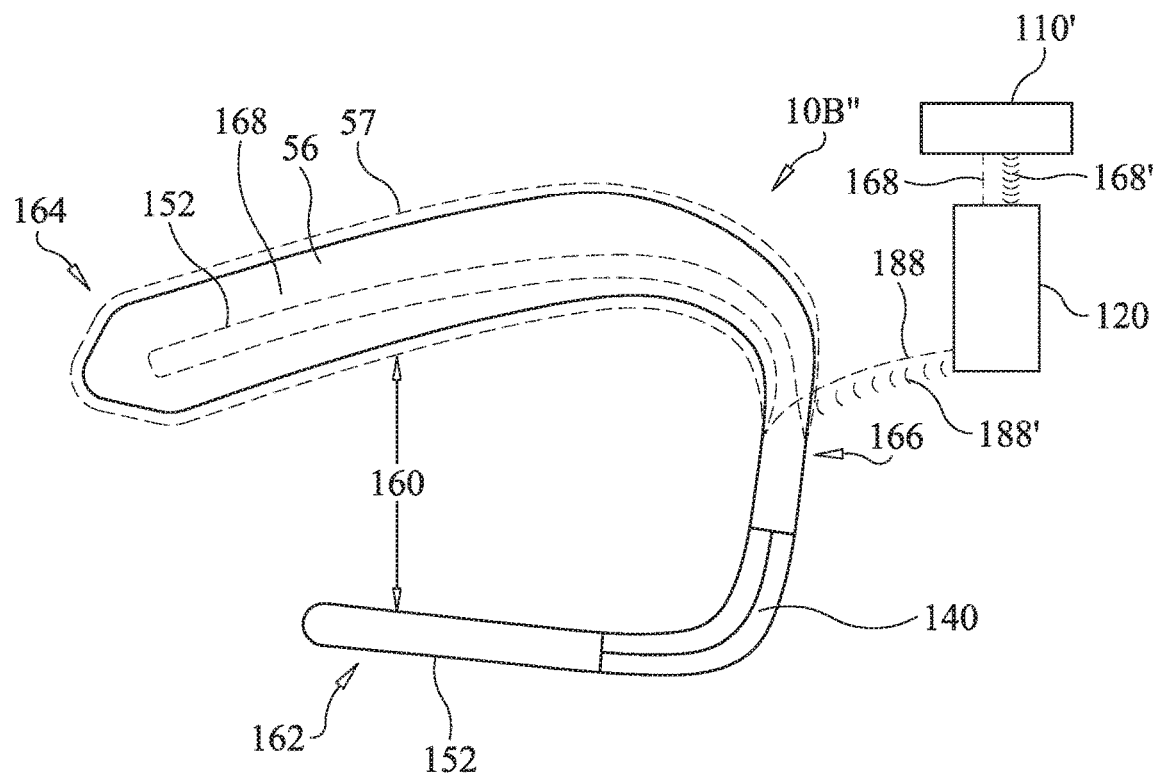
FIG. 22B illustrates another variation according to an embodiment of the present invention.

FIG. 22B schematically illustrates a variation, wherein device 10B" includes actuating subsystem 140, while a sensing device 110' is provided separately of the device 10B" just as in FIG. 22A above, and so will not be further described here. A controlling subsystem 120" is provided separately of the device 10B" and is configured to receive input from sensing device 110', process the input received and send control signals to the actuating subsystem 140, either wirelessly 188' or by wire 188, in the same manner as described above for embodiments where the controlling subsystem is integrated in the device. The controlling subsystem 120" is preferably implanted, but could be provided as an external unit to be used outside of the patient, where it could be worn by the patient, for example. All other external features described above with regard to the variation of FIG. 22A may optionally be included with the variation of FIG. 22B.

Figure 22C:
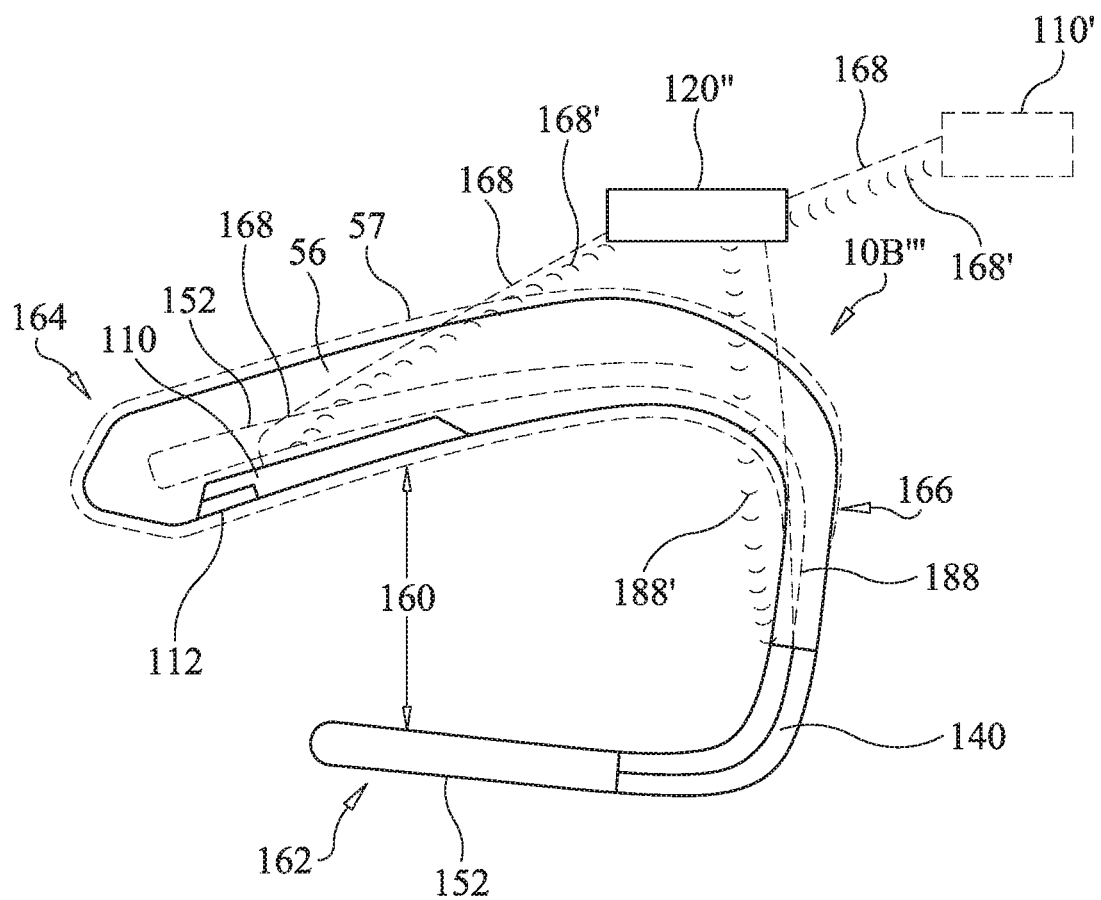
FIG. 22C illustrates another variation according to an embodiment of the present invention.

FIG. 22C illustrates a variation wherein device 10B''' is provided with an integrated sensing subsystem 110 and an integration actuation subsystem 140. A controlling subsystem 120" is provided separately of the device 10B''' and is configured to receive input from sensing subsystem 110, either by wired 168 or wireless 168' communication, process the input received and send control signals to the actuating subsystem 140, either wirelessly 188' or by wire 188, in the same manner as described above for embodiments where the controlling subsystem is integrated in the device. Optionally an external sensor 110' may be provided that the controlling system is configured to receive input from, either wirelessly 168' or by wire 168. External sensor 110' may be from another device, or any of the options described above with regard to the variation of FIG. 22A. The controlling subsystem 120" is preferably implanted, but could be provided as an external unit to be used outside of the patient, where it could be worn by the patient, for example. All other external features described above with regard to the variation of FIG. 22A may optionally be included with the variation of FIG. 22C.

As noted, a device according to the present invention could be configured to communicate with another device that is not part of the system of the present invention, such as another implant that can sense or monitor for data that could be inputted to the system of the present invention and used for deciding whether to actuate the device. Further alternatively input could be from a device that is external to the body, either as a result of monitoring, or as signals that could be manually inputted to the system of the present invention by a user outside the body in which the system is implanted. The system of the present invention could be configured to receive any combination of these types of inputs and use them in deciding whether to actuate the device. In the case of manual inputs from an external source, the system could be configured so that the manual inputs could override the decision making process of the controlling subsystem, so that the actuating subsystem could be directly controlled by the manual input. Although the variants in FIGS. 22A-22C have been shown and described as variants of device 10B in FIG. 7A, it is noted that any of these variations can be applied to any of the embodiments of devices 10 described herein.

While the present invention has been described with reference to the specific embodiments thereof, it should be understood by those skilled in the art that various changes may be made and equivalents may be substituted without departing from the true spirit and scope of the invention. For example, the invention can be used in other target tissues or organs, such as other valves of the heart, pulmonary tissues, the gastrointestinal system (including, but not limited to the stomach, small intestine, and/or large intestine), renal system, urinary system or any other tissues/organs that may be effectively treated with direct mechanical manipulation.

Further alternatively, a device can be separated into different sensing, controlling/power generation, and actuation modules that can be located in different aspects of the anatomy and/or target tissue/organs. Still further a device can be powered and communicated with via direct lead means by placing the controlling/power generation module(s) subcutaneously.

In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A device configured to be attached to a surface of a tissue or organ using a minimally-invasive procedure, said device comprising:
    a main body having a device surface adapted to be contacted to the tissue or organ;
    a sensor on or in said device surface adapted to sense a signal characteristic of a function of tissue or organ;
    an actuator in a portion of said main body which, when actuated, changes a conformation of said main body; and
    a controller configured to receive said signal, process said signal, and, control actuation of said actuator when it is determined that an unacceptable condition of functioning of the tissue or organ is occurring;
    wherein said sensor comprises an audio sensor configured to receive audio signals generated by functioning of the tissue or organ, and wherein said controller compares an audio signature of the tissue or organ characterized by electrical signals converted from the audio signals received by said audio sensor, with a normal audio signature characteristic of the tissue or organ with normal function, to determine whether to actuate said actuator.

2. An epicardial device for reducing or preventing regurgitation of blood through a valve of a heart, said device comprising:
    a main body having a surface adapted to be contacted to an epicardial surface of the heart;
    a sensor on or in said surface adapted to sense a signal characteristic of a function of the valve;
    an actuator in a portion of said main body which, when actuated, changes a conformation of said main body; and
    a controller configured to receive said signal, process said signal, and, control actuation of said actuator when it is determined that an unacceptable level of regurgitation is occurring;
    wherein said sensor comprises an audio sensor configured to receive audio signals generated by functioning of the valve, and wherein said controller compares an audio signature of the valve characterized by electrical signals converted from the audio signals received by said audio sensor, with a normal audio signature characteristic of a valve with no regurgitation, to determine whether to actuate said actuator.

3. An epicardial device for reducing or preventing regurgitation of blood through a valve of a heart, said device comprising:
    a main body having a surface adapted to be contacted to an epicardial surface of the heart;
    a sensor on or in said surface adapted to sense a signal characteristic of a function of the valve;
    an actuator in a portion of said main body which, when actuated, changes a conformation of said main body; and
    a controller configured to receive said signal, process said signal, and, control actuation of said actuator when it is determined that an unacceptable level of regurgitation is occurring;
    wherein said sensor comprises an electrical sensor configured to receive electrical signals generated by functioning of the valve or heart, and wherein said controller compares said electrical signals from said electrical sensor with a normal electrical signal characteristic of normal functioning of the valve with no regurgitation, to determine whether to actuate said actuator.

4. The epicardial device of claim 2 configured for reshaping an annulus of a mitral valve of the heart.

5. The epicardial device of claim 2 configured for reshaping an annulus of a tricuspid valve of the heart.

6. The epicardial device of claim 2, wherein said controller is configured to process said signal received from said sensor and control actuation of said actuator in real time.

7. The epicardial device of claim 2, wherein said sensor, said actuator and said controller are all contained in said main body.

8. The epicardial device of claim 2, wherein said sensor comprises a motion sensor;
    wherein said motion sensor converts motion applied thereagainst by the epicardial surface of the heart in contact with said motion sensor, to an electrical signal characterizing said motion.

9. The epicardial device of claim 2, wherein said sensor comprises a motion sensor;
    wherein said motion sensor converts motion applied thereagainst by the epicardial surface of the heart in contact with said motion sensor, to an electrical signal for motion-driven electric power generation.

10. The epicardial device of claim 9, wherein said controller includes an energy conversion unit that converts said electrical signal from said motion sensor to electrical energy having requisite characteristics for charging an energy storage unit to power said controller and said actuator.

11. The epicardial device of claim 2, further comprising an electrical sensor configured to receive electrical signals generated by functioning of the valve or heart, and wherein said controller compares said electrical signals from said electrical sensor with a normal electrical signal characteristic of normal functioning of the valve with no regurgitation, to determine whether to actuate said actuator.

12. The epicardial device of claim 2, wherein said actuator comprises a bi-metallic, resistively heated actuator.

13. The epicardial device of claim 2, wherein said actuator comprises an expandable chamber.

14. The epicardial device of claim 2, wherein said actuator is motor driven.

15. The epicardial device of claim 2, wherein said main body comprises an anterior segment adapted to be contacted to an anterior surface of the heart, a posterior segment adapted to be contacted to a posterior surface of the heart and a lateral segment joining said anterior segment and said posterior segment.

16. The epicardial device of claim 15, further comprising an inferior segment extending from said main body in a direction transverse to a plane in which said anterior, lateral and posterior segments extend.

17. The epicardial device of claim 15, further comprising a second actuator located in said inferior segment.

18. The device of claim 1, wherein said controller is configured to process said signal received from said sensor and control actuation of said actuator in real time.

19. The device of claim 1, wherein said sensor, said actuator and said controller are all contained in said main body.

20. The device of claim 1, further comprising a motion sensor;
    wherein said motion sensor converts motion applied thereagainst by the tissue or organ in contact with said motion sensor, to an electrical signal for motion-driven electric power generation; and wherein said controller includes an energy conversion unit that converts said electrical signal from said motion sensor to electrical energy having requisite characteristics for charging an energy storage unit to power said controller and said actuator.

21. The device of claim 20, wherein said motion sensor further converts motion applied thereagainst by the tissue or organ to an electrical signal characterizing said motion.

22. The device of claim 1, wherein said actuator comprises a bi-metallic, resistively heated actuator.

23. The device of claim 1, wherein said actuator comprises an expandable chamber.

* * * * *